(12) United States Patent
Yatagai et al.

(10) Patent No.: US 7,823,782 B2
(45) Date of Patent: Nov. 2, 2010

(54) DENTAL OPTICAL COHERENCE TOMOGRAPH

(75) Inventors: Toyohiko Yatagai, Nagareyama (JP); Yoshiaki Yasuno, Tsukuba (JP); Masami Tamura, Kyoto (JP)

(73) Assignee: Shofu Inc., Kyoto (JP)

( * ) Notice: Subject to any disclaimer, the term of this patent is extended or adjusted under 35 U.S.C. 154(b) by 365 days.

(21) Appl. No.: 12/085,423

(22) PCT Filed: Nov. 22, 2006

(86) PCT No.: PCT/JP2006/323279
§ 371 (c)(1), (2), (4) Date: May 22, 2008

(87) PCT Pub. No.: WO2007/060973
PCT Pub. Date: May 31, 2007

(65) Prior Publication Data
US 2009/0079993 A1 Mar. 26, 2009

(30) Foreign Application Priority Data
Nov. 22, 2005 (JP) .............................. 2005-337372

(51) Int. Cl.
*G06K 7/10* (2006.01)
(52) U.S. Cl. .................................................. 235/454
(58) Field of Classification Search ............... 235/439, 235/454; 356/497
See application file for complete search history.

(56) References Cited

U.S. PATENT DOCUMENTS 6,377,349 B1 4/2002 Fercher
6,637,656 B2 * 10/2003 Kurogama et al. ..... 235/462.25
6,813,030 B2 * 11/2004 Tanno ........................ 356/497
2002/0196438 A1 12/2002 Kerschbaumer et al.
2008/0024788 A1 1/2008 Shimizu et al.

FOREIGN PATENT DOCUMENTS

| JP | 11-325849 | 11/1999 |
|---|---|---|
| JP | 2001-59714 | 3/2001 |
| JP | 2002-310897 | 10/2002 |

(Continued)

OTHER PUBLICATIONS

Haruna, et al., "Technical Development of Optical Coherence Tomography for Clinical Application", Laser Review, Oct. 2003, pp. 654-662.

(Continued)

*Primary Examiner*—Seung H Lee
(74) *Attorney, Agent, or Firm*—Hamre, Schumann, Mueller & Larson, P.C.

(57) ABSTRACT

A dental optical coherence tomography apparatus for measuring tissue in a stomatognathic region of a living body or an artificial composition in the stomatognathic region as a measured object includes: a variable wavelength light source (15); a light splitting portion (19) that splits light-source light emitted from the variable wavelength light source (15) into reference light (29) and measuring light (28); an interference portion (19) that causes the measuring light (28) and the reference light (29) to interfere with each other, thereby generating interference light; a photodetection portion (41) that measures the interference light; and an arithmetic portion (27b) that generates an image of a measured object (22) by Fourier transforming or inverse Fourier transforming the intensity of the interference light, whose wavelength changes with time, that has been detected by the photodetection portion for each of the wavelengths. Accordingly, an optical coherence tomography apparatus applicable to dental measurement can be provided.

10 Claims, 22 Drawing Sheets

FOREIGN PATENT DOCUMENTS

| | | |
|---|---|---|
| JP | 2003-329577 | 11/2003 |
| JP | 2004-167080 | 6/2004 |
| JP | 2004-347380 | 12/2004 |
| JP | 2005-283155 | 10/2005 |

OTHER PUBLICATIONS

Fried, et al., "Imaging caries lesions and lesion progression with polarization sensitive optical coherence tomography", Journal of Biomedical Optics, vol. 7, No. 4, Oct. 2002, pp. 618-627.

Colston, et al., "Imaging of hard- and soft-tissue structure in the oral cavity by optical coherence tomography", Applied Optics, vol. 37, No. 16, Jun. 1998, pp. 3582-3585.

Colston, et al., "Dental OCT", Optics Express, vol. 3, No. 6, Sep. 1998 pp. 230-238.

Feldchtein, et al., "In vivo OCT imaging of hard and soft tissue of the oral cavity", Optics Express, vol. 3, No. 6, Sep. 1998, pp. 239-250.

* cited by examiner

|  | Area | Thickness | Shape | Reflectance (relative value) |
|---|---|---|---|---|
| Enamel layer | Upper part of gum | 0.8~1.2 mm | • Curved toward inner side of tooth | 0.05 |
|  | Lower part of gum | 0.5~0.8 mm | • Linear in tooth axis direction<br>• Curved toward inner side of tooth in plane perpendicular to tooth axis | 0.05 |
|  | Dental root portion | 0 ⇒ Changing to cementum layer |  | 0.05 |
| Dentine layer | Upper part of gum | 1.5~2 mm | • Curved toward inner side of tooth | 0.15 |
|  | Lower part of gum | 0.5~0.8 mm | • Linear in tooth axis direction<br>• Curved toward inner side of tooth in plane perpendicular to tooth axis | 0.15 |
|  | Dental root portion | 0.3~0.5 mm | • Parallel to shape of dental root | 0.3 |
| Cementum layer | Dental root portion | 0.1~0.2 mm | • Parallel to shape of dental root |  |
| ..... | ..... | ..... | ..... | ..... |
| Alveolar bone | ..... | ..... | ..... | ..... |

FIG. 6

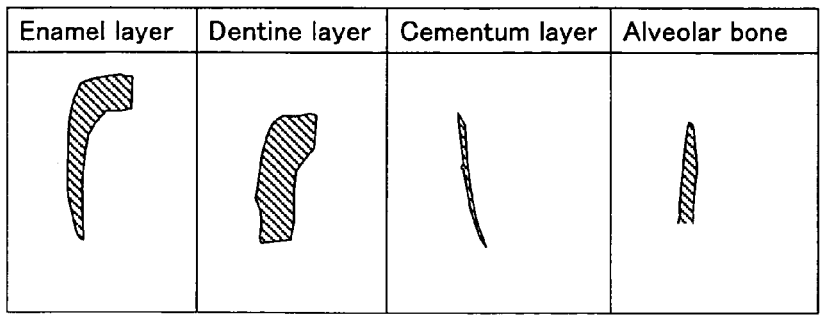

FIG. 7

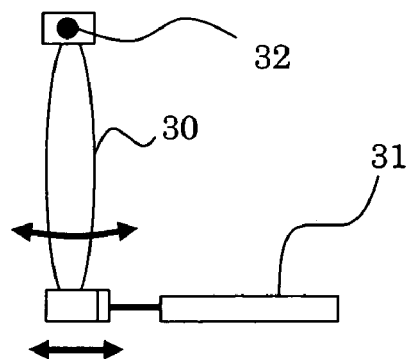
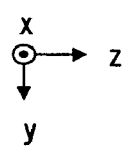
FIG. 9
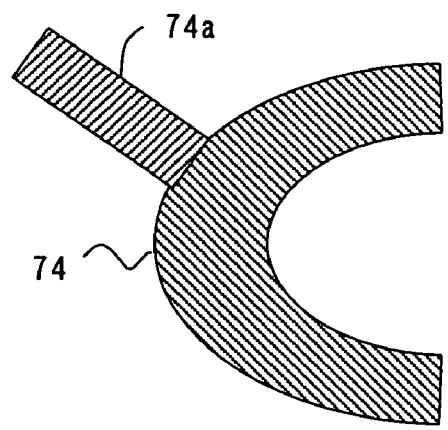
FIG. 10

DENTAL OPTICAL COHERENCE TOMOGRAPH

TECHNICAL FIELD

The present invention relates to an apparatus for optical coherence tomography (tomographic measurement using low-coherence light as a probe), which is a nondestructive tomographic measurement technique. In particular, the invention relates to an optical coherence tomography apparatus applicable to dental measurement.

BACKGROUND ART

Conventionally, for dental diagnoses, X-ray imaging apparatuses, intraoral cameras, dental cameras, X-ray CT, MRI, etc. have been used in order to image the stomatognathic region.

Images obtained with X-ray imaging apparatuses ultimately are transmitted images, and the information of the subject along the traveling direction of X rays is detected in an overlapped manner. Therefore, the internal structure of the subject cannot be known in a three-dimensional way. In addition, since X rays are harmful to the human body, the annual exposure dose is limited, and they can be handled only by qualified experts. Moreover, they can be used only in chambers surrounded by shielding members such as lead and lead glass.

Intraoral cameras image only the surface of intraoral tissues, and the internal information such as the information about a tooth therefore cannot be obtained. Like X-ray imaging apparatuses, X-ray CT is harmful to the human body. Moreover, it has low resolution, and involves large and expensive apparatuses. MRI has low resolution, and involves large and expensive apparatuses. Moreover, it cannot image the internal structure of a tooth containing no moisture.

Incidentally, an optical coherence tomography apparatus (hereinafter, referred to as "OCT apparatus") is harmless to the human body, and can obtain the three-dimensional information of subjects with high resolution. Therefore, it is applied in the field of ophthalmology, such as for tomographic measurements of a cornea or a retina, (for example, see JP2003-329577A, JP2002-310897A, JP11-325849A, and JP2001-059714A). It should be noted that OCT is the abbreviation for optical coherence tomography. The optical coherence tomography apparatus also may be called an optical interference tomography apparatus.

Here, a conventional OCT apparatus will be described. FIG. 30 is a diagram showing the configuration of a conventional OCT apparatus. In an OCT unit 1 constituting the OCT apparatus shown in FIG. 30, the light emitted from a light source 2 is collimated by a lens 3, and then split into reference light 6 and measuring light 5 by a beam splitter 4. The measuring light 5 passes through a galvano mirror 8, and is focused by a lens 9 on a measured object 10, where the measuring light 5 is scattered and reflected. Thereafter, the measuring light 5 again passes through the lens 9, the galvano mirror 8 and the beam splitter 4, and is focused on a photodetector 14 by a lens 7. Meanwhile, the reference light 6 passes through a lens 12, is reflected at a reference mirror 13, and passes through the lens 12 and the beam splitter 4 again. Thereafter, the reference light 6 overlaps the measuring light 5, enters the lens 7, and is focused on the photodetector 14.

The light source 2 is a low-temporal-coherence light source. Those components of light emitted from a low-temporal-coherence light source at different time points tend not to interfere with one another. Therefore, an interference signal will appear only when the distance of the optical path through which the measuring light 5 passes is substantially equal to the distance of the optical path through which the reference light 6 passes. Accordingly, the reflectance distribution of the measured object 10 in the depth direction (the z axis direction) can be obtained by measuring the intensity of the interference signal with the photodetector 14, while moving the reference mirror 13 in the direction of the optical axis of the reference light 6 and thus changing the difference in the optical path length between the measuring light 5 and the reference light 6. That is, the configuration of the measured object 10 in the depth direction can be determined by sweeping the optical path length difference.

The measuring light 5 reflected in the z axis direction at the measured object 10 carries the object information of the measured object 10 in the waveform of its electromagnetic wave. However, there is no photodetector capable of directly measuring the waveform on the temporal axis, because the optical waveform of the measuring light 5 is a phenomenon that is very rapid. Therefore, the OCT apparatus causes the measuring light 5 reflected at the measured object 10 and the reference light 6 to interfere with each other, thereby converting the reflection property information of each area of the measured object 10 into a change in the intensity of the interference light. As a result, the photodetector 14 can perform the detection on the temporal axis.

A two-dimensional cross-sectional image of the measured object 10 can be obtained by performing scanning in the transverse direction (the x-axis direction) with the galvano mirror 8, in addition to the scanning in the depth direction (the z-axis direction) of the measured object with the reference mirror 13. With such an OCT apparatus, measurement can be performed with high resolution in the order of several micrometers. Accordingly, with the OCT apparatus, a high resolution image of the interior of a living body can be obtained in a nondestructive and contactless manner.

With regard to the application of the OCT apparatus to the field of the dentistry, examples are disclosed in which tomographic images of teeth are taken using OCT apparatuses (for example, see Documents 1 to 5 below).

Document 1: LASER KENKYU, October 2003: Technical development of the optical coherence tomography centering on medical science Document 2: Journal of Biomedical Optics, October 2002, Vol. 7 No. 4: Imaging caries lesions and lesion progression with polarization sensitive optical coherence tomography Document 3: APPLIED OPTICS, Vol. 37, No. 16, and 1 Jun. 1998: Imaging of hard-and soft-tissue structure In the oral cavity by optical coherence tomography Document 4: OPTICS EXPRESS, Vol. 3, No. 6, and 14 Sep. 1998: Dental OCT Document 5: OPTICS EXPRESS, Vol. 3, No. 6, and 14 Sep. 1998: In vivo OCT Imaging of hard and soft tissue of the oral cavity

DISCLOSURE OF INVENTION

Problem to be Solved by the Invention

However, in practice, OCT apparatuses are not used for dental medical examinations. At least at present, it is not practical to use OCT apparatuses for dental diagnosis, and no dental OCT apparatus is available as a product. The reason is that, with an OCT apparatus, imaging is time consuming since it is necessary to perform two-dimensional mechanical scanning including the depth direction in order to obtain a single tomographic image. Moreover, the apparatuses are complex and expensive, and have poor durability. That is, it has been difficult to apply the OCT apparatuses to dental measurement in practice.

Therefore, in view of the above-described problems, it is an object of the present invention to provide an optical coherence tomography apparatus having a simple structure, capable of performing high-speed imaging and being applicable to dental measurements.

Means for Solving Problem

A dental optical coherence tomography apparatus according to the present invention is a dental optical coherence tomography apparatus for measuring tissue in a stomatognathic region of a living body or an artificial composition in the stomatognathic region as a measured object, the apparatus including: a variable wavelength light source that emits light whose wavelength changes with time within a predetermined range; a light splitting portion that splits light-source light emitted from the variable wavelength light source into reference light for irradiating a reference mirror and measuring light for irradiating a measured object; an interference portion that causes the measuring light reflected at the measured object and the reference light reflected at the reference mirror to interfere with each other, thereby generating interference light; a photodetection portion that measures the interference light, whose wavelength changes with time within a predetermined range; and an arithmetic portion that generates reflection property data representing a position at which the measuring light is reflected at the measured object and the reflection intensity thereof by Fourier transforming or inverse Fourier transforming an intensity of the interference light measured by the photodetection portion in each stage of the changing wavelength, and that generates an image of the measured object.

Effects of the Invention

According to the present invention, it is possible to provide an optical coherence tomography apparatus having a simple structure, capable of performing high speed imaging and being applicable to dental measurements.

BRIEF DESCRIPTION OF DRAWINGS

FIG. 6 shows an example of the data structure of a collection of dental shape rules.

FIG. 7 shows an example of the shapes represented by the data contained in a dental shape library.

FIG. 9 is a conceptual diagram illustrating an exemplary method in which a lens is driven.

FIG. 10 shows another example of the configuration of a mouthpiece and a mouthpiece holder.

DESCRIPTION OF THE INVENTION

Figure 1:
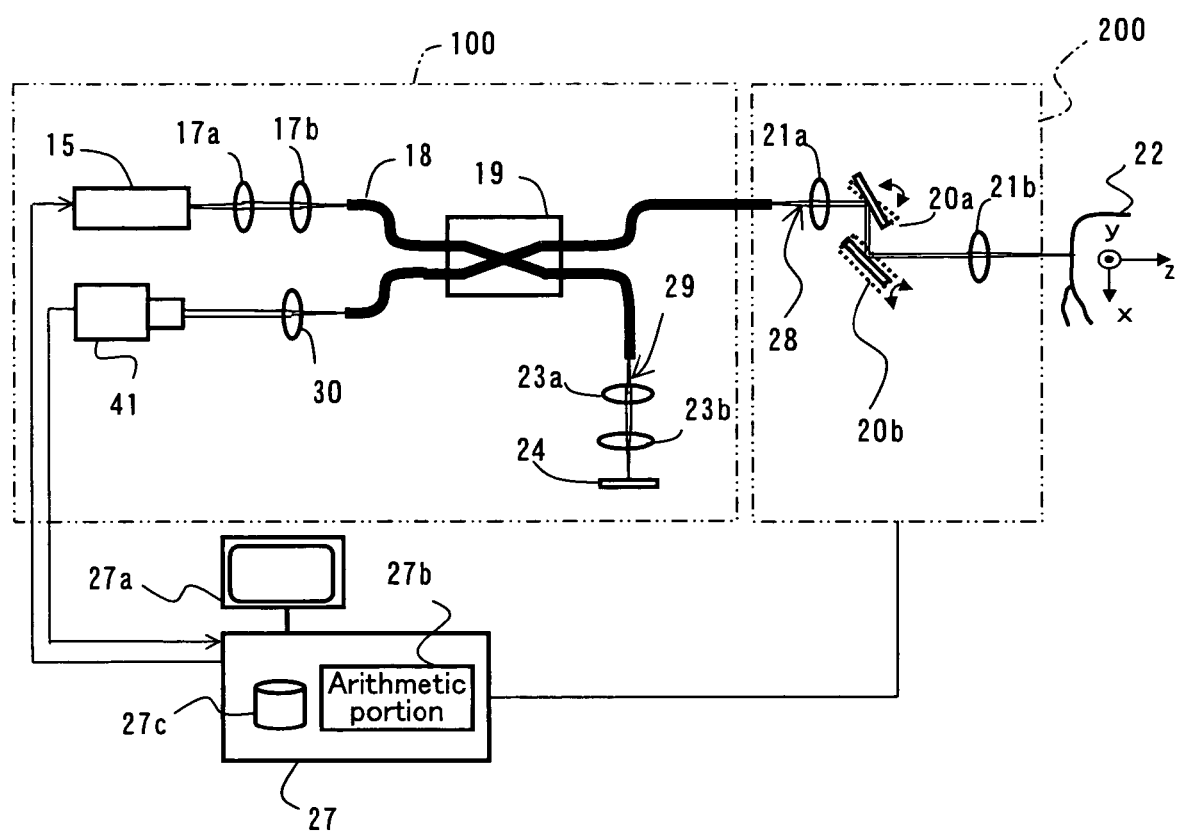
FIG. 1 is a diagram showing an example of the configuration of an FD-OCT apparatus according to Embodiment 1.

A dental optical coherence tomography apparatus according to the present invention is a dental optical coherence tomography apparatus for measuring tissue in a stomatognathic region of a living body or an artificial composition in the stomatognathic region as a measured object, the apparatus including: a variable wavelength light source that emits light whose wavelength changes with time within a predetermined range; a light splitting portion that splits light-source light emitted from the variable wavelength light source into reference light for irradiating a reference mirror and measuring light for irradiating a measured object; an interference portion that causes the measuring light reflected at the measured object and the reference light reflected at the reference mirror to interfere with each other, thereby generating interference light; a photodetection portion that measures the interference light, whose wavelength changes with time within a predetermined range; and an arithmetic portion that generates reflection property data representing a position at which the measuring light is reflected at the measured object and the reflection intensity thereof by Fourier transforming or inverse Fourier transforming an intensity of the interference light measured by the photodetection portion in each stage of the changing wavelength, and that generates an image of the measured object. In the dental optical coherence tomography apparatus according to the present invention, since light whose wavelength changes with time within a predetermined range is emitted from the variable wavelength light source, the photodetection portion can detect the interference light, whose wavelength changes with time within a predetermined range. That is, the photodetection portion detects the interference light intensity in each stage of the changing wavelength. Accordingly, the photodetection portion detects the distribution of wavelength of the interference light. The arithmetic portion Fourier transforms or inverse Fourier transforms the interference light intensity in each stage of the changing wavelength, thereby converting it into the data representing the reflection intensity at each of the reflected positions of the measuring light in the measured object. Accordingly, the arithmetic portion can generate reflection property data representing a position at which the measuring light is reflected at the measured object and the reflection intensity thereof. The arithmetic portion generates a tomographic image of the measured object, using the reflection property data. That is, the arithmetic portion can obtain the information of the measured object in the depth direction based on the data of the interference light of each of the wavelengths.

Accordingly, it is possible to obtain the information of the measured object in the depth direction without performing mechanical scanning in the direction of the measuring light, i.e., the depth direction of the measured object. As a result, the apparatus has a simplified structure, and can perform imaging at high speed. Furthermore, it is possible to place the OCT apparatus next to a dentist's chair, making it possible to perform dental measurement using the OCT apparatus. That is, it is possible to provide an OCT apparatus that can be applied to dental diagnosis.

It is preferable that a beam splitter or a fiber coupler is used for both of the functions of the light splitting portion and the interference portion.

A dental optical coherence tomography apparatus according to the present invention is a dental optical coherence tomography apparatus for measuring tissue in a stomatognathic region of a living body or an artificial composition in the stomatognathic region as a measured object, the apparatus including: a light source; a light splitting portion that splits light-source light emitted from the light source into reference light for irradiating a reference mirror and measuring light for irradiating a measured object; an interference portion that causes the measuring light reflected at the measured object and the reference light reflected at the reference mirror to interfere with each other, thereby generating interference light; a photodetection portion that measures the interference light; an arithmetic portion that generates reflection property data representing a position at which the measuring light is reflected at the measured object and the reflection intensity thereof based on the interference light measured by the photodetection portion, and generates an image of the measured object; a probe that radiates the measuring light so that the measuring light is guided to the measured object, receives the measuring light reflected at the measured object, and guides the aforementioned measuring light to the interference portion; and a fixing means that is fixed to the probe and is able to fix a relative position between the probe and the measured object by being in contact with a portion of the measured object or by being bonded thereto via an adhesive member.

Since the probe radiates the measuring light so that the measuring light is guided to the measured object, receives the measuring light reflected at the measured object, and guides the aforementioned measuring light to the interference portion, it is possible to radiate the measuring light to a measured area having a complex structure, which is the measured object, in the stomatognathic region, and receive the reflected light.

In addition, the relative position between the probe and the measured object is fixed in a state in which the fixing means is fixed to the probe, and is in contact with the measured object or bonded to the measured object via the adhesive member. Accordingly, with the use of the probe, the irradiation position of the measuring light can be changed flexibly in accordance with the shape of the measured object, and fix the relative position between the probe and the measured object.

In the dental optical coherence tomography apparatus according to the present invention, it is preferable that the probe includes an objective lens that focuses the measuring light on the measured object, and the fixing member fixes a relative position between the probe and the measured object so that a focal point of the measuring light focused by the objective lens is located on a surface or the interior of the measured object, in a state in which the fixing member is in contact with the measured object.

When the fixing member is in contact with measured object, the position and orientation of the probe relative to the measured object is fixed so that the focal point of the objective lens is located on the measured object. Accordingly, the measurer can keep the probe in the position and the orientation that are suitable for measurement by holding the probe so that the fixing member is in contact with the measured object.

In the dental optical coherence tomography apparatus according to the present invention, it is preferable that the fixing means comprises a mouthpiece having a shape that can be inserted between upper dentition and lower dentition, or a splint core including a mounting portion that is attachable to an adhesive member is mounted that has a shape matching the shape of dentition including a measured object, or. Thus, the relative position between the probe and the measured object is fixed in a stable manner.

In the dental optical coherence tomography apparatus according to the present invention, it is preferable that the probe further includes a scanning means that scans the measuring light for irradiating the measured object in directions perpendicular to the optical axis of the measuring light. Since the probe is provided with the scanning means, it is possible to perform two-dimensional scanning or three-dimensional scanning in the oral cavity where the measured object is located.

In the dental optical coherence tomography apparatus according to the present invention, it is preferable that the arithmetic portion generates reflection property data representing a depth of the measuring light entering the measured object and the reflection intensity of the measuring light at the aforementioned depth based on the interference light, and corrects the reflection intensity in accordance with the aforementioned depth zp, or a function or an integral function relating to the aforementioned depth zp, thereby generating a tomographic image of the measured object in an optical axis direction.

The intensity of the measuring light decreases with an increase of the depth of the measured object in the optical axis direction, so that the intensity of the reflecting light also decreases. As a result, the reflection intensity of the measuring light in the position at the depth zp, represented by the reflection property data, tends to decrease with an increase of the depth zp. Therefore, it is possible to reduce the decrease of the reflection intensity by the influence of the depth by correcting the reflection intensity represented by the reflection property data in accordance with the depth zp, or a function or an integral function relating to the depth zp.

In the dental optical coherence tomography apparatus according to the present invention, it is preferable that the arithmetic portion generates reflection property data representing a distribution of reflection intensity of the measuring light in the depth direction of the measuring light entering the measured object based on the interference light, divides the distribution of the reflection intensity into a plurality of layers in the aforementioned depth direction, and correct the reflection intensity for each of the aforementioned layers by using a transmittance of each of the divided layers to, thereby generating a tomographic image of the measured object in an optical axis direction.

In the case where the measured object has a plurality of layers having different light transmittances, the degree of the decrease in the reflection intensity of the measuring light with the depth varies between the layers. Since the arithmetic portion uses the light transmittance of each of the divided layers to correct the reflection intensity for each of the layers, in the case where the measured object has a plurality of layers having different light transmittances, it is possible to perform correction taking into consideration the difference in the decrease of the reflection intensity between the layers. One example of the measured object having a plurality of layers with different light transmittances is a tooth. A tooth includes the enamel layer, the dentine layer, the cementum layer, the alveolar bone and so on.

In the dental optical coherence tomography apparatus according to the present invention, it is preferable that the light source includes two or more light sources having different center wavelengths, and includes a light source switching portion that guides light from any one of the two or more light sources to the light splitting portion. This makes it possible to select the light of a wavelength suitable for the constituents of the measured object as the light-source light.

It is preferable that the dental optical coherence tomography apparatus according to the present invention further includes: a dental shape data recording portion for recording dental shape data indicating the shape of each area of tissue in a stomatognathic region of a living body; and a display portion for displaying an image generated by the arithmetic portion, wherein the arithmetic portion extracts a portion of the generated image that represents each area, a lesion, a prosthetic appliance or a filling in the tissue in the stomatognathic region, using the dental shape data, and outputs the aforementioned portion to the display portion in such a manner that the aforementioned portion can be distinguished visually from other portions.

The arithmetic portion can extract a portion of the above-described image indicating the shape of each area, a lesion, a prosthetic appliance or a filling in the tissue in the stomatognathic region based on the dental shape data indicating the shape of each area of the tissue in the stomatognathic region. By the arithmetic portion outputting each of these extracted portions to the display portion in such a manner that each of these portions can be distinguished visually from other portions, an operator looking at that display easily can recognize the shape of each area, a lesion, a prosthetic appliance or a filling in the tissue in the stomatognathic region.

A dental optical coherence tomography apparatus according to the present invention is a dental optical coherence tomography apparatus for measuring tissue in a stomatognathic region of a living body or an artificial composition in the stomatognathic region as a measured object, the apparatus including: a light source; a light splitting portion that splits light-source light emitted from the light source into reference light for irradiating a reference mirror and measuring light for irradiating a measured object; an interference portion that causes the measuring light reflected at the measured object and the reference light reflected at the reference mirror to interfere with each other, thereby generating interference light; a photodetection portion that measures the interference light; an arithmetic portion that generates reflection property data representing a position at which the measuring light is reflected at the measured object and the reflection intensity thereof based on the interference light measured by the photodetection portion, and that generates an image of the measured object; a probe that radiates the measuring light so that the measuring light is guided to the measured object, receives the measuring light reflected at the measured object, and guides the measuring light to the interference portion; a rotating member that is attached to the probe so that it can rotate about at least one direction as a rotation axis, and that includes an irradiation port for radiating the measuring light in a direction forming a fixed angle or a variable angle with the rotation axis; and a driving portion that rotates the rotating member.

Since the irradiation direction of the measuring light radiated from the irradiation port to the measured object forms a fixed angle or a variable angle with the rotation axis of the rotating member, rotation of the rotating member causes the position of the measuring light radiated to the measured object to move in the direction of that rotation. Accordingly, when the rotating member is rotated by the driving portion, the measuring light radiated from the irradiation port of the rotating member is scanned in the direction of that rotation.

It is preferable that the dental optical coherence tomography apparatus according to the present invention further includes: a sleeve provided on the rotating member via a bearing so that the sleeve covers the rotating member, and including a window for allowing passage of the measuring light radiated from the irradiation port.

By fixing the position of the window of the sleeve relative to the measured object, the relative position between the sleeve and the measured object is fixed. Since the sleeve is provided so that it covers the rotating member via the bearing, the rotating member rotates in the sleeve whose position is fixed. That is, the relative position between the rotating member and the measured object is also fixed. Accordingly, it is possible to subject the measured object to scanning in one direction in a stable manner.

It is preferable that the dental optical coherence tomography apparatus according to the present invention further includes a polarization manipulation portion that manipulates the polarization condition of at least one of the light-source light, the reference light, the measuring light and the interference light.

In the dental optical coherence tomography apparatus according to the present invention, since the polarization manipulation portion manipulates the polarization condition of at least one of the light radiated from the light source to the light splitting portion, the reference light, the measuring light and the interference light, it is possible to obtain an image reflecting the polarization property or the birefringence property of the measured object. As a result, it is possible to observe oral tissue, including, for example, initial dental caries, the dentine, the enamel, gums and the alveolar bone, which have unique polarization properties or unique birefringence properties.

It is preferable that dental optical coherence tomography apparatus according to the present invention further includes a cylindrical lens or a cylindrical mirror that shapes the cross section of the measuring light into the shape of a line aligned in one direction in a plane perpendicular to the irradiation direction of the measuring light.

"Cylindrical lens" refers to a lens that functions as a lens only in one of the two directions at a right angle to the optical axis. Only the shape of the cross section in the direction in which a cylindrical lens functions as a lens has a typical lens shape including a curved contour, and the shape of the cross section in the direction in which a cylindrical lens does not function as a lens may be, for example, rectangular.

"Cylindrical mirror" refers to a mirror that functions as a lens only in one of the two directions at a right angle to the optical axis. Only the shape of the cross section in the direction in which a cylindrical mirror functions as a lens has a typical lens shape including a curved contour, and the shape of the cross section in the direction in which a cylindrical mirror does not function as a lens may be, for example, rectangular.

The cylindrical lens or the cylindrical mirror shapes the cross section of the measuring light in a plane at a right angle to the optical axis into the shape of a line aligned with the direction of one axis in a plane perpendicular to the irradiation direction of the measuring light. Accordingly, the measuring light is radiated so that it is distributed in the direction of the above-described one axis of the measured object. That is, the measuring light is focused on a line in the above-described one axis direction in the measured object. Accordingly, it is possible to measure the cross section of the measured object in the direction of the above-described one axis, without performing mechanical scanning in the direction of the above-described one axis.

In the dental optical coherence tomography apparatus according to the present invention, it is preferable that at least one of the light-source light, the measuring light, the reference light, the interference light and light divided into a spectrum is guided with an optical fiber. With the use of an optical fiber, the traveling direction of light can be changed flexibly. In that case, an optical fiber in which a plurality of optical fibers are aligned parallel to one another, or an optical fiber bundle that is bundled so that its cross section perpendicular to the optical axis has a substantially circular shape may be used.

It is preferable that the dental optical coherence tomography apparatus according to the present invention is configured to project the measuring light or a pattern of visible light onto the surface of the measured object, and monitors the surface image of the measured area using a two-dimensional imaging apparatus, or to record such an image synchronously with a measured tomographic image. This allows the operator to confirm the measured area during measurement.

Hereinafter, embodiments of the present invention will be described with reference to the drawings.

Embodiment 1

FIG. 1 is a diagram showing an example of the configuration of a Fourier domain optical coherence tomography apparatus (hereinafter referred to as "FD-OCT apparatus") according to Embodiment 1. It should be noted that FD-OCT is the abbreviation for Fourier-domain OCT. An FD-OCT apparatus is an OCT apparatus that measures interference light between measuring light emitted from a low-coherent light source and reflected at an measured object, and reference light emitted from the light source and reflected at the reference mirror, and determines the optical properties of the measured object in the depth direction, i.e., the direction of the optical axis of the measuring light from the information of the interference light, using Fourier transformation or inverse Fourier transformation. With the FD-OCT apparatus, mechanical scanning in the direction of the optical axis of the measuring light becomes unnecessary. There are at least two kinds of FD-OCT apparatuses, namely, the swept source FD-OCT and the spectral domain FD-OCT. In this embodiment, the swept source FD-OCT will be described.

Here, the spectral domain FD-OCT apparatus is an OCT apparatus that is characterized by detecting a spectrum resulting from separating interference light with a diffraction grating, and determining the information about the measured object in the direction of the optical axis of the measuring light from this spectrum, using Fourier transformation or inverse Fourier transformation.

Example of Structure of FD-OCT (Swept Source Type) According to this Embodiment

As shown in FIG. 1, the swept source FD-OCT apparatus includes an OCT unit 100, a probe unit 200 and a calculating machine 27. The OCT unit 100 is provided with a light source 15, a fiber coupler 19, a reference mirror 24 and a photodetector 41. The probe unit 200 is provided with galvano mirrors 20a and 20b, as well as lenses 21a and 21b. The calculating machine 27 is connected to the light source 15, the photodetector 41 and the galvano mirrors 20. The calculating machine 27 may be, for example, a computer such as a personal computer, and includes at least an arithmetic portion 27b such as a CPU, and a recording portion 27c such as a hard disk. The calculating machine 27 also may include, for example, a display portion 27a such as a liquid crystal panel, a CRT and a PDP.

It should be noted that the configuration of the OCT unit 100, the probe unit 200 and the calculating machine 27 is not limited to the configuration shown in FIG. 1. For example, the function of the calculating machine 27 can be incorporated in the OCT unit 100.

The light source 15 is a temporally and spatially low-coherent light source. That is, it is a light source that emits light whose wavelengths are distributed over a narrow range around a center wavelength. The center wavelength of the light radiated by the light source 15 changes with time. The wavelength of the light radiated by the light source 15 changes within a wavelength range unique to the apparatus, for example, for every fixed period of time. That is, the light radiated from the light source 15 sweeps the wavelength of the above-described range for every fixed period of time.

As the light source 15, a narrowband laser light source of adjustable wavelength, such as a tunable LD (laser diode), can be used, for example. The light source 15 may be, for example, a light source that radiates light whose center wavelength changes within the variation range of ±110 nm or ±55 nm with respect to the center wavelength of 830 nm, 1100 nm, 1300 nm, 1500 nm or 1600 nm. In addition, the light source 15 may emit light whose wavelength changes by 0.064 nm in 17 nanoseconds (17 nsec), for example. That is, the light source 15 can divide the wavelength variation range of 110 nm into 1700 points, and emit light while the wavelength is changed by one point with a frequency of 60 MHz.

The fiber coupler 19 is an example of an optical interferometric apparatus that performs the function of a light splitting portion and an interference portion. The optical interferometric apparatus is an input-output switchable optical component that causes two input lights to interfere with each other, and outputs them in two directions. Examples of the optical interferometric apparatus include a beam splitter and a half mirror, in addition to the fiber coupler 19.

The photodetector 41 is an example of the photodetection portion. As the photodetector 41, a photodiode can be used, for example. In particular, an infrared photodiode is suitable as the photodetector 41. In the swept source FD-OCT apparatus, the light detected by the photodetector 41 is of zero dimension, that is, a light ray.

In the spectral domain FD-OCT apparatus, the light detected by the photodetector 41 is light that has been spectrally separated with a diffraction grating, and thus extends in one dimension. Therefore, a high-resolution photodetection array of one or more dimensions is needed as the photodetector 41. One example of a high-resolution photodetection array of one or more dimensions is a CCD image sensor. However, CCD image sensors, especially those with a 1.3 μl infrared region, are complex, large, and expensive. In comparison, the photodiodes used for the photodetector 41 of the swept source FD-OCT apparatus are simple, small, and inexpensive. This will be a highly advantageous effect for applying the swept source FD-OCT apparatus to dentistry.

The probe unit 200 includes the lenses 21a and 21b, and the galvano mirrors 20a and 20b. The measuring light 28 output by the fiber coupler 19 of the OCT unit 100 is guided and radiated to the measured object 22, whereas the reflected component of the measuring light 28 reflected at the measured object 22 is received and guided to the fiber coupler 19. The details of the configuration of the probe unit 200 will be described later. The probe unit 200 and the OCT unit 100 are connected to each other with an optical fiber 18, and light transmission between the probe unit 200 and the OCT unit 100 is carried out using the optical fiber 18. Thus, the probe unit 200 can be formed as a different casing from the OCT unit 100. That is, the position and orientation of the probe unit 200 can change flexibly according to the condition of the measured object 22, without any constraints from the position and orientation of the OCT unit 100. Furthermore, the movable range of the probe unit 200 increases.

Preferably, the probe unit 200 is configured to be operable by an operator in a hand-held manner. This makes it possible for the operator to use the unit easily from the side of a dentist's chair. The operator can use the OCT apparatus in a condition in which the positional relationship between the probe unit 200 and the patient is flexible.

When applying the OCT apparatus to dental use, it is predicted that the OCT apparatus is used on the side of the chair on which the patient usually sits at the time of medical examination. In this case, if an air-based optical system (in which the optical path to the probe unit transverses the air instead of in the optical fiber) is used to position the probe unit 200, then the entire OCT unit needs to be positioned in the oral cavity of the patient precisely. Moreover, it is unrealistic that the operator would manipulate a comparatively heavy OCT held in his/her hand.

Example of Operations of FD-OCT Apparatus

Next, the operations of the FD-OCT apparatus shown in FIG. 1 will be described. In this embodiment, a case is described where the measured object 22 is tissue in the stomatognathic region of a living body, or an artificial composition in the stomatognathic region. In the following description, a coordinate system is defined as follows. As shown in FIG. 1, for the measured object 22, the z direction is defined as the direction of the optical axis of the measuring light 28, i.e., the depth direction of the measured object 22, and the x-y plane is defined as the plane perpendicular to the z direction. The y direction is defined as the scanning direction of the galvano mirror 20b, and the x direction is defined as the direction that is perpendicular to the y direction and is the scanning direction of the galvano mirror 20a. In the locations other than the measured object 22, the x, y, and z directions are defined as the corresponding x, y, and z directions of the measured object 22. "Optically corresponding" means that, even if the spatial direction is changed by the mirrors, the lenses, the optical fiber and so on, the z direction is the traveling direction of light, the y direction is the scanning direction of the galvano mirrors and so on, and the x direction is the direction perpendicular to both the y and z directions.

The light emitted from the light source 15 is collimated by lenses 17a and 17b, and then split into the reference light 29 and the measuring light 28 by the fiber coupler 19. The measuring light 28 passes through the optical fiber 18, the lens 21a, and the galvano mirrors 20a and 20b, and then is focused on the measured object 22 by the lens 21b. The measuring light 28 is reflected and scattered at and transmitted through the measured object 22. Of the measuring light reflected and scattered at and transmitted through the measured object 22, those components that have been reflected or backscattered (hereinafter simply referred to as "reflected light") are again passed through the lens 21b, the galvano mirrors 20a and 20b, the lens 21a, the optical fiber 18 and the fiber coupler 19, and guided to the photodetector 41 by a lens 30.

Meanwhile, the reference light 29 passes through the optical fiber 18, and the lenses 23a and 23b, is reflected at the reference mirror 24, again passes through the lenses 23a and 23b, and is caused to interfere with the reflected component of the measuring light 28 by the fiber coupler 19, so that it enters the lens 30 in a manner overlapping the reflective component of the measuring light 28, and is guided to the photodetector 41.

Since the measuring light 28 and the reference light 29 are both light whose wavelength changes with time, the light that interferes at the fiber coupler 19 and is guided to the photodetector 41 also has a wavelengths that changes with time. In other words, the photodetector 41 detects the interference light between the reflected component of the measuring light 28 and the reference light 29 for a plurality of wavelengths. The interference light with various wavelengths measured by the photodetector 41 is Fourier transformed or inverse Fourier transformed by the arithmetic portion 27b in the calculating machine 27, thereby obtaining a correlation between the measuring light 28 and the reference light 29. From this correlation, the data representing the position of the measured object 22 in the depth direction (z-axis direction) and the intensity of the reflected light at that position are obtained. That is, the reflectance property of the measured object 22 is obtained. From this reflectance property, information relating to the structure, the composition, or the optical properties of the measured object 22 is acquired. For example, the arithmetic portion 27b of the calculating machine 27 generates a cross-sectional image of the measured object 22 based on the measured interference light. An example of the processing in which the arithmetic portion 27b of the calculating machine 27 generates a cross-sectional image will be described later.

With the above-described FD-OCT apparatus, it is not necessary to move the reference mirror 24 to adjust the optical path lengths of the measuring light 28 and the reference light 29, and to perform scanning in the z-axis direction. That is, the information relating to the structure of the measured object 22 in the depth direction (z-axis direction) can be obtained, without performing any mechanical manipulation in the z-axis direction. With the FD-OCT apparatus, tomographic information in which the S/N ratio has been improved compared with those obtained by conventional apparatuses can be obtained. Consequently, a high-resolution tomographic image can be obtained. Moreover, since penetration (the degree of reach) is higher than in conventional apparatuses, it is possible to observe deeper locations inside the measured object.

As described above, the swept source FD-OCT apparatus is an OCT apparatus that obtains the internal information of the measured object in the z-axis direction based on the interference light between the measuring light 28 and the reference light 29 at various wavelengths.

In order to obtain a three-dimensional cross-sectional image of the measured object 22, it is necessary to perform scanning in the y-axis direction and the x-axis direction, in addition to the z-axis direction. In this embodiment, the scanning in the y-axis direction is performed by driving the galvano mirror 20b, and the scanning in the x-axis direction is performed by driving the galvano mirror 20a.

As described above, with the swept source FD-OCT apparatus, the structure of the measured object 22 in the z-axis direction can be determined from the interference light for the wavelengths that change with time, so that it is not necessary to perform mechanical scanning for obtaining a tomographic image of the measured object 22. As a result, the apparatus has a simplified structure, and can perform imaging at high speed. Furthermore, the basic properties such as capability of quantatively obtaining three-dimensional internal information of the measured object, as well as other superior properties such as noninvasiveness and high resolution of the OCT apparatus can be utilized in the field of dentistry.

That is, in the field of dentistry, the measured object is often hard tissue such as a tooth and an alveolar bone. Since hard tissue such as a tooth and an alveolar bone causes strong scattering, it has been difficult to observe with conventional OCT apparatuses. By using an FD-OCT apparatus that realizes higher penetration than conventional OCT apparatuses for dental applications, it is possible to observe deeper locations inside hard tissue such as a tooth and an alveolar bone.

Figure 2:
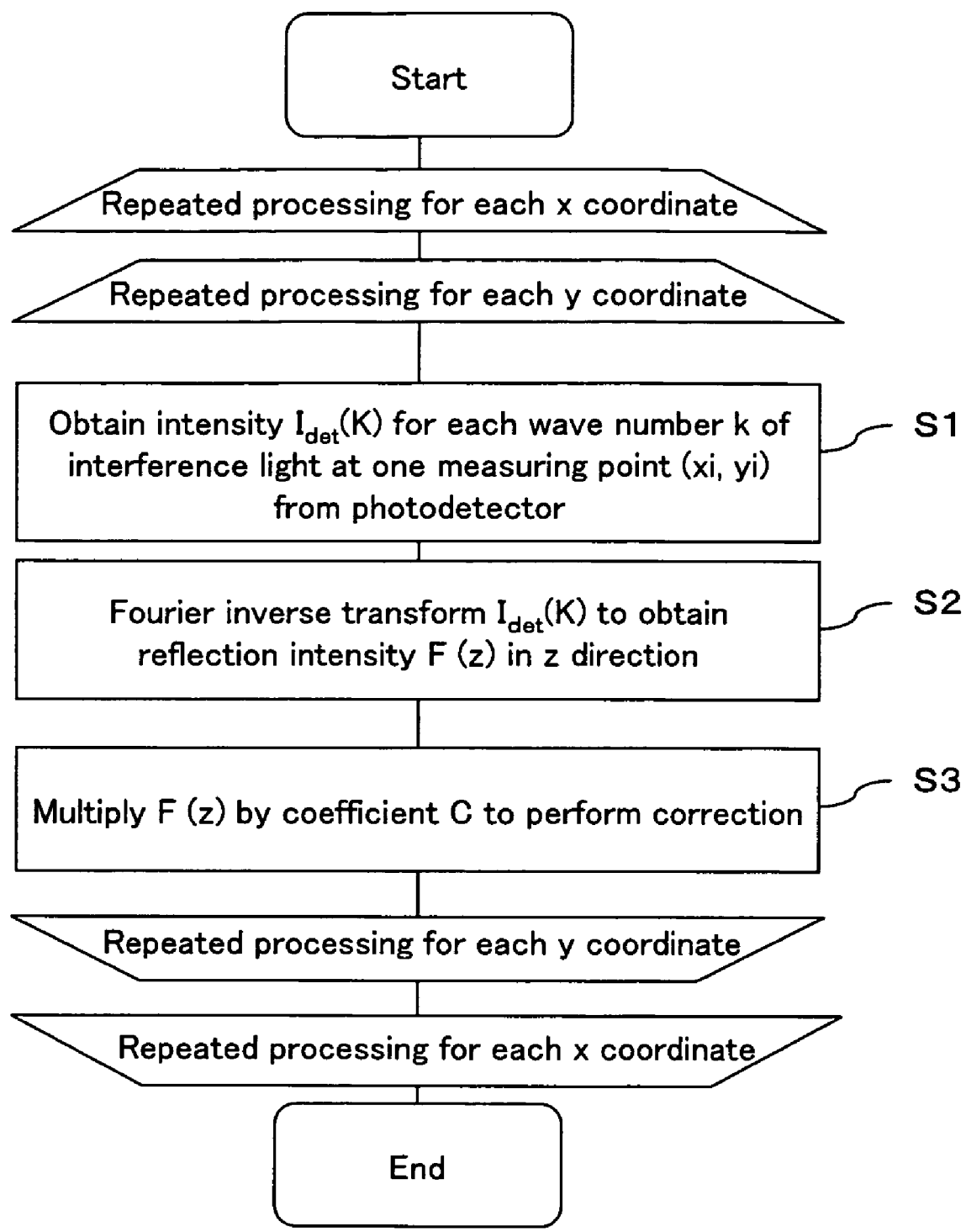
FIG. 2 is a flowchart showing an example of the processing in which an arithmetic portion generates a cross-sectional image based on measured interference light.

Example of the Processing in which the Arithmetic Portion 27b of the Calculating Machine 27 Generates a Cross-sectional Image FIG. 2 is a flowchart showing an example of the processing in which the arithmetic portion 27b of the calculating machine 27 generates a cross-sectional image based on measured interference light. In the example shown in FIG. 2, the processing of Steps S1 to S3 is repeated for each set of x-y coordinates. In Steps S1 to S3, the arithmetic portion 27b determines the reflection intensity distribution in the z-axis direction at one measurement point represented by coordinates (xi, yi), for example. The arithmetic portion 27b first obtains the intensity for each wavelength of the interference light detected by the photodetector 41 (Step S1). For example, the arithmetic portion 27b obtains, from the photodetector 41, a value obtained by converting the intensity of the interference light between the component of the measuring light 28 that was reflected at the coordinates (xi, yi) and the reference light 29 into a current. Here, the current $i_{det}$ (k) representing the intensity of the interference light with the wave number k (=2π/wavelength) that is output by the photodetector 41 can be expressed, for example, by Equation (1) below.

$$i_{det}(k) = \frac{\eta q}{h\nu}\left(P_r + P_0 \int r^2(z)dz + 2\sqrt{P_r P_0} \int r(z)\Gamma(z)\cos\{2k(t)z + \phi(z)\}dz\right) \quad (1)$$

η: Sensitivity of the photodiode
q: Elementary electron charge (=1.6×10$^{-19}$ coulomb)
hν: Photon energy (ν represents the frequency)
$P_r$: Reference light intensity
$P_0$: Detection light intensity
r (z): Intensity profile of the light reflection coefficient in the z direction of the subject
φ (z): Phase profile of the light reflection coefficient in the z direction of the subject
Γ (z): Coherence function of light-source light
k (t):=2π/λ (t) Wave number of light-source light (scanned by the light source 15)

In Equation (1) above, the third term expresses the light intensity resulting from interference between the reference light 29 and the reflected component of the measuring light 28. The first term and the second term represent the background light intensity, not resulting from the interference. In addition, although the first term and the second term are canceled by inverse Fourier transformation described below, they influence the dynamic range and noise of the detection system.

In Equation (1) above, the wave-number k (t) of the light-source light changes depending on time t. That is, the light source 15 scans the wave number k by changing the wave number k of the light-source light with Time t. The photodetector 41 can output the time series data of the current idet (k) representing the intensity of interference light, in synchronization with the scanning of the wave number k by the light source 15.

The arithmetic portion 27b determines the reflection intensity distribution F (z) of the measuring light 28 in the z-axis direction in the measured object 22 based on the data output from the photodetector 41 (Step S2). For example, the arithmetic portion 27b can determine the signal of the reflected component of the measuring light 28 at the depth z, i.e., the reflection intensity distribution F (z) by inverse Fourier transforming the time series data of idet (k) output by the photodetector 41. For example, F (z) can be determined by inverse Fourier transformation using Equation (2) below.

$$F(z) = \int i_{det}(k)\exp(2\pi jkz)dk \quad (2)$$

idet (k) is detected by the photodetector 41 as a discrete value idet ($k_m$) for each wave number $k_m$ (m=0, 1, 2 . . . ) that changes with time. Accordingly, the arithmetic portion 27b also can determine the value F ($Z_l$) representing the reflection intensity at the depth $Z_l$ (l=0, 1, 2 . . . ) by discrete inverse Fourier transformation (discrete inverse Fourier transformation), for example, using Equation (3) below.

$$F(z_l) = \frac{\Delta k}{N_S}\sum_{m=0}^{N_S-1}\{i_{det}((k_m)\exp(2\pi jk_m z_l)\} \quad (3)$$

m: the DFT (discrete Fourier transform) discretization number of the wave number k
l: the DFT (discrete Fourier transform) discretization number at the depth z
Δk: the scan width of the wave number of the light source In addition, the operation using Equations (1) to (3) can be used not only for the swept source FD-OCT apparatus but also for the spectral domain FD-OCT apparatus. Moreover, it is preferable that the arithmetic portion 27b uses the well-known fast Fourier transformation algorithm when discrete inverse Fourier transforming the data obtained from the photodetector 41. Next, the arithmetic portion 27b corrects the signal at the depth z, i.e., the value F (z) representing the reflection intensity, in accordance with the depth z (Step S3). The arithmetic portion 27b also may correct F (zp), for example, by multiplying the reflection intensity F (zp) by the correction coefficient C (zp) at the depth zp, expressed by any one of Equations (4), (5), (6) or (7) below.

$$C(zp) = \left(\frac{\int_0^{zp} F(z)dz}{F(zp)}\right)^2 \quad (4)$$

$$C(zp) = \frac{\int_0^{zp} F(z)dz}{\int_0^{z} F(z)dz} \quad (5)$$

$$C(zp) = \frac{\int_0^{zp} F(z)dz}{F(zp)} \quad (6)$$

$$C(zp) = \left(\frac{\int_0^{zp} F(z)dz}{\int_0^{z} F(z)dz}\right)^2 \quad (7)$$

Here, although the correction coefficient C (zp) may be zero, this means that, when representing an image based on the corrected data, the brightness of that location becomes the reference value, and it does not necessarily have to mean that the brightness becomes zero (becomes deep-black). Equations (4) to (7) may be such that the attenuation of the measuring light in the depth direction can be corrected, and do not necessarily have to represent the brightness of the final image. In addition, the equations for correction are not limited to Equations (4) to (7), and the correction does not necessarily have to be performed using a value given by an equation. Correcting the intensity in the depth direction itself is of significance.

The magnitude of the measuring light 28 that reaches the depth z of the measured object of the OCT apparatus decreases with an increase in the reflection intensity of light at a depth of 0 to z. The measuring light 28 that has reached the depth z of the measured object is backscattered or reflected with a reflectance R unique to that area, and returns to the surface of the measured object, while attenuating between a depth of 0 to zp(s), and is detected as a reflected component of the measuring light 29 at the depth z. Accordingly, correction can be performed in accordance with the depth zp, for example, by multiplying the reflection intensity F (zp) at the depth zp by a correction coefficient C (zp) determined with the value representing the reflected light intensity at a depth of 0 to zp using any one of Equations (4) to (7) above.

The arithmetic portion 27b repeatedly performs the processing of Step S1 to S3 described above for each set of x-y coordinates. For example, when the galvano mirror 20b scans with y=0 to 10000 (μm) in the y-axis direction and the photodetector 41 measures interference light at intervals of 1 μm, it is preferable to repeat the processing of S1 to S3 above for each y coordinate wherein yi=0, 10, 20 . . . 10000 (μm). Likewise, when the galvano mirror 20a scans with x=0 to 10000 (μm) in the x-axis direction and the photodetector 41 measures interference light at intervals of 10 μm, it is preferable to repeat the processing of S1 to S3 above for each x coordinate wherein xi=0, 10, 20 . . . 10000 (μm).

Thus, the arithmetic portion 27b can obtain a three-dimensional image of the measured object by determining the reflection intensity distribution in the z direction for each set of x-y coordinates in the scanning range. The arithmetic portion 27b can generate, for example, an image representing a two-dimensional cross-sectional tomographic view (so-called "B-scan"). Furthermore, the arithmetic portion 27b can obtain three-dimensional subject information (so-called "C-scan") from a plurality of tomographic views represented by the B-scan.

Since the basic principle of the OCT apparatus is such that light reflected at a certain depth is extracted and used as measurement information, not only the intensity of the measuring light itself used for diagnosis, but also the intensity of the reflected light decreases as the depth increases. That is, the intensity of the measured information decreases in inverse proportion to the square of the integral value of the transmittance of light. Consequently, when converting the measured information of the OCT apparatus directly into an image, if identical tissues are located at different depths, they will not be imaged with the same brightness. This is diagnostic information that is difficult to judge by those experts and persons making a diagnosis who are used to seeing conventional X-ray images.

As such, the OCT apparatus operates under the basic principle that both the measuring light and the reflected light attenuate as the depth of an area of observed tissue increases. Accordingly, the deeper the area to be measured, the more severe the influence of noise becomes.

By correcting the reflection intensity in Step S3 above with the arithmetic portion 27b, it is possible to alleviate the defective condition resulting from a reflection intensity that decreases with the depth as described above. In addition, the method of correcting the reflection intensity is not limited to the above-described example.

Modification of the Correction Processing

Figure 3:
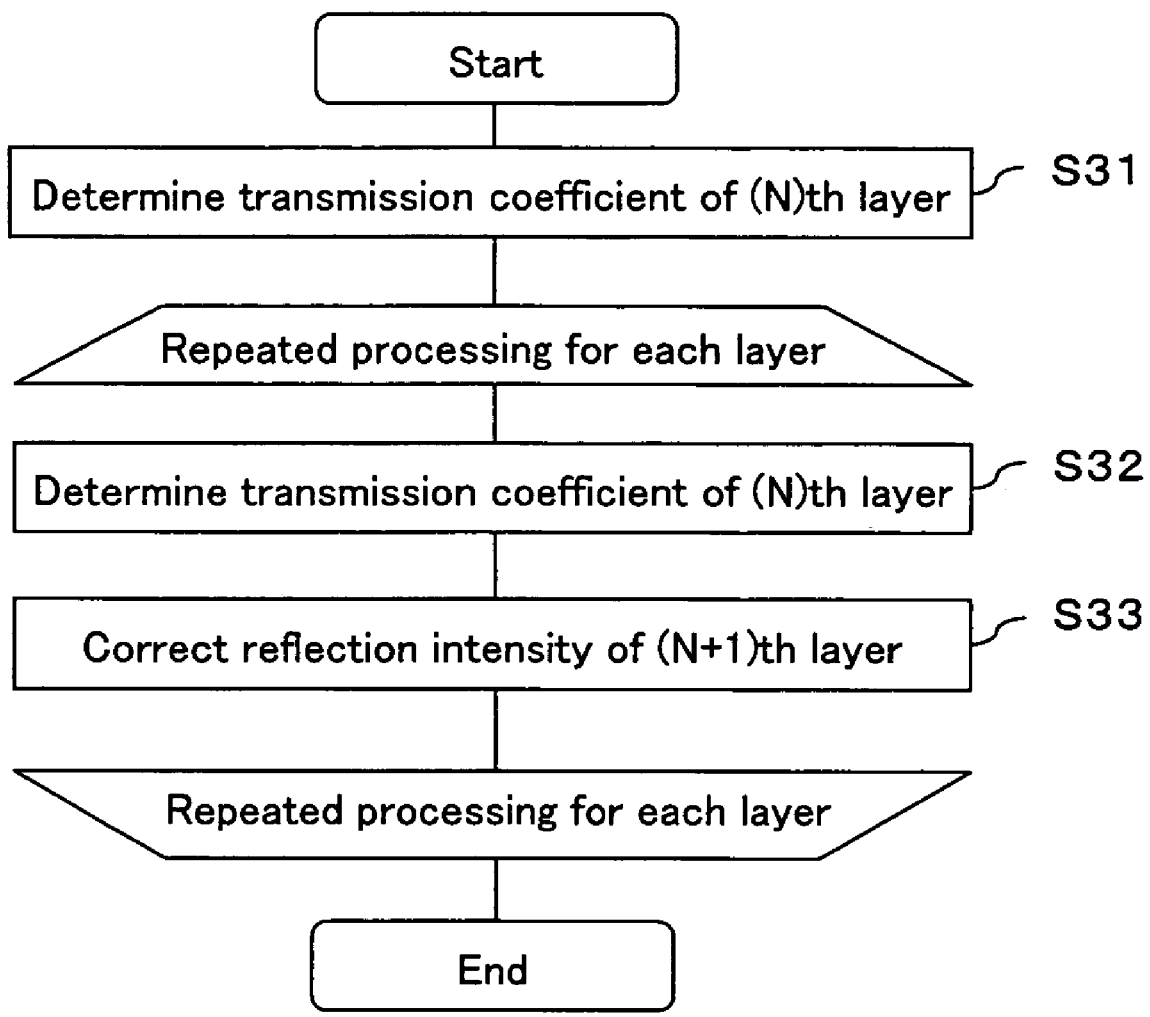
FIG. 3 is a flowchart showing a flow of the processing of correcting the reflection intensity layer by layer.

Although the above-described example of the correction processing shows an example of the correction using the depth zp or an integration function relating to the depth zp, the arithmetic portion 27b also can divide the reflection intensity distribution in the depth direction into a plurality of layers, and correct the reflection intensity layer by layer, using the transmission coefficient representing the light transmittance (=attenuation factor) of each layer, for example. FIG. 3 is a flowchart showing a flow of the processing of correcting the reflection intensity layer by layer.

Figure 4:
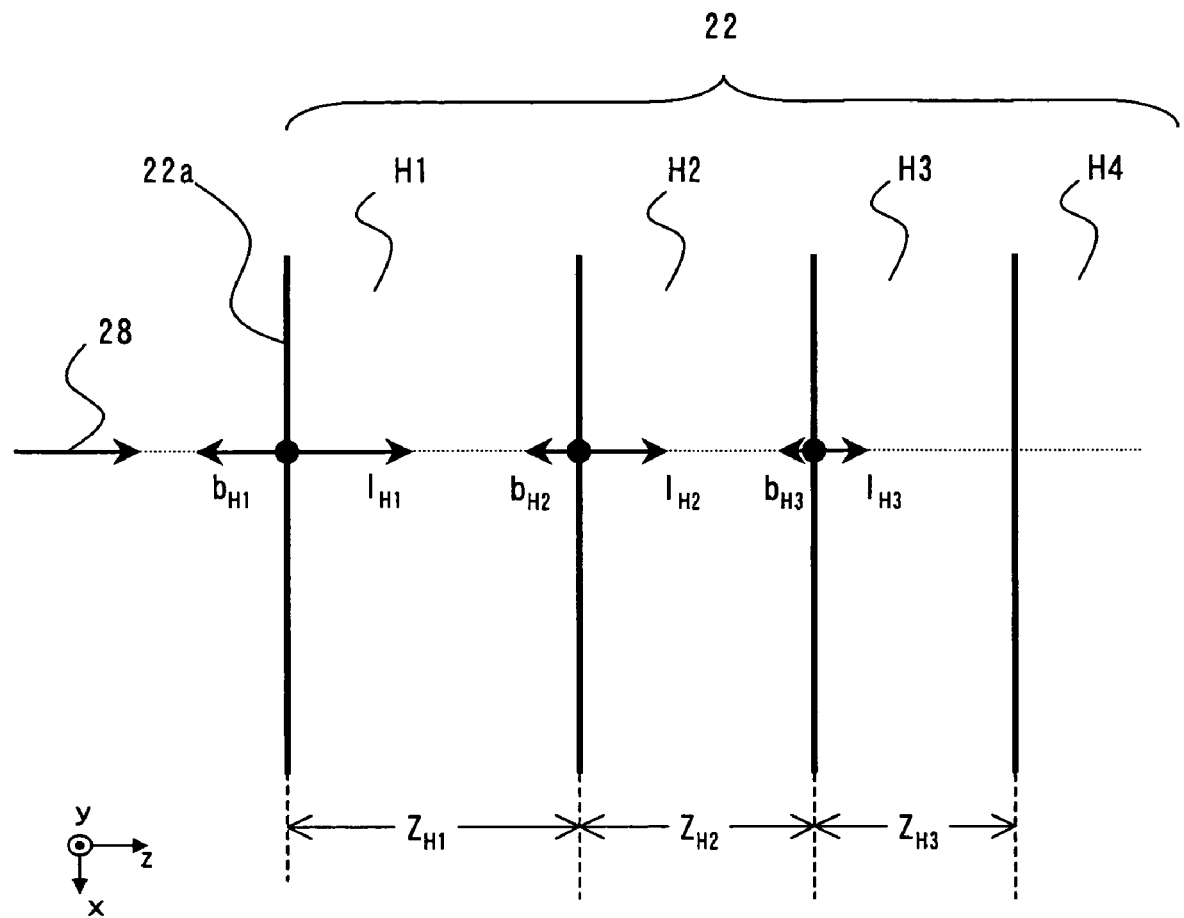
FIG. 4 shows an example in which the reflection intensity distribution in the depth direction is divided into a plurality of layers.

As shown in FIG. 3, the arithmetic portion 27b divides the reflection intensity distribution in the depth direction into a plurality of layers (Step S31). FIG. 4 shows an example in which the reflection intensity distribution in the depth direction is divided into a plurality of layers. In the example shown in FIG. 4, a layer H1, a layer H2, a layer H3 and a layer H4 are present in this order in the depth direction from a surface 22a from which the measuring light 28 enters the measured object 22.

In the case where the measured object 22 is a tooth, the arithmetic portion 27b can divide the positions corresponding, for example, to the enamel layer, the dentine layer, the cementum layer and the alveolar bone layer of the tooth as the layer H1, the layer H2, the layer H3 and the layer H4, respectively. That is, a region having the same properties can be divided as a single layer. For example, the arithmetic portion 27b can divide a region having the same identical properties as a single layer by dividing the reflection intensity distribution in the depth direction into a plurality of layers, with a location where the reflection intensity has changed suddenly as the boundary.

The arithmetic portion 27b determines the transmission coefficient for the first layer H1, which is directly under the surface 22a (Step S32). In the layer H1, when the intensity of the measuring light 28 entering from the surface 22a is $I_{H1}$, the intensity $I'_{H1}$ of the transmitted light transmitted through the layer H1 of the light incident on the layer H1 is expressed by Equation (8) below.

$$I'_{H1} = I_{H1} e^{-\mu_{H1} z_{H1}} \tag{8}$$

Then, the arithmetic portion 27b can calculate the transmission coefficient μH1 of the first layer H1 using the brightness $b_{H1}$ representing the reflection intensity at the surface 22a, the brightness $b'_{H1}$ representing the reflection intensity at the deepest part of the layer H1 and the depth $Z_{H1}$ of the layer H1, for example, using Equation (9) below.

$$\mu_{H1} = -\frac{1}{z_{H1}} \log\left(\frac{b'_{H1}}{b_{H1}}\right) \tag{9}$$

It should be noted that the method of determining the transmission coefficient $\mu_{H1}$ is not limited to the method using Equation (9) above. For example, it is possible to calculate the transmission coefficient at a plurality of positions with different depths within the layer H1 using the brightness at different positions, instead of using the brightness $b'_{H1}$ representing the reflection intensity at the deepest part in Equation (9) above, and use their average value as the transmission coefficient in the layer H1. Alternatively, it is also possible to determine the transmission coefficient of suitable adjacent regions in a plane perpendicular to the depth direction, and use their average value as the transmission coefficient. This is an effective method for removing artifacts. For example, artifacts appearing in a linear or belt-like fashion in the direction of the measuring light in a measured image obtained by the OCT apparatus can be removed by performing the below-described correction processing using the average value of the transmission coefficients in a direction perpendicular to the depth direction.

Since the intensity $I'_{H1}$ of the transmitted light transmitted through the layer H1 is equal to the intensity $I_{H2}$ of the incident light entering the layer H2, $I_{H2}$ can be expressed by Equation (10) below.

$$I_{H2} = I_{H1} e^{-\mu_{H1} z_{H1}} \tag{10}$$

Next, the arithmetic portion 27b corrects the reflection intensity of the second layer H2 using the transmission coefficient in the first layer H1 (Step S33). For example, the arithmetic portion 27b can calculate $B_{H2}$ using Equation (11) below using the brightness $b_{H2}$ representing the reflection intensity at the outermost surface within the layer H2, based on Equation (10) above, and correct the brightness of the layer H2 to $B_{H2}$.

$$B_{H2} = \frac{I_{H1}}{I_{H2}} b_{H2} = b_{H2} e^{\mu_{H1} z_{H1}} \tag{11}$$

Similarly, the arithmetic portion 27b repeats the processing of Steps S32 and S33 for the layer H2 and the layer H3. That is, the arithmetic portion 27b repeats the process (Step S32) of determining the transmission coefficient of the layer H2, and the process (Step S33) of correcting the reflection intensity of the layer H3. Thus, the reflection intensity is corrected for the second and further layers. In addition, the brightness $B_{H1}$ of the first layer H1 is corrected to $B_{H1} = b_{H1}$ using the brightness $b_{H1}$ at the outermost surface of the layer H1 based on the above description.

The transmission coefficient used for the correction process of Step S33 may not necessarily be determined by calculation. For example, it is also possible to record the value of the transmission coefficient layer by layer in the recording portion 27c beforehand, and perform the correction process using these values.

The thickness of each of the layers may not necessarily be the characteristic thickness of the measured object. For example, although the thickness of the enamel is about 0.5 to 2 mm, this may be divided into 5 to 20 layers each having a thickness of 0.1 mm. In this case, unlike the actual enamel, artifacts that change gradually occur in the brightness of each layer, and this may be smoothed by first-order linear or second-order parabolic smoothing.

Example of Image Display

Figure 5:
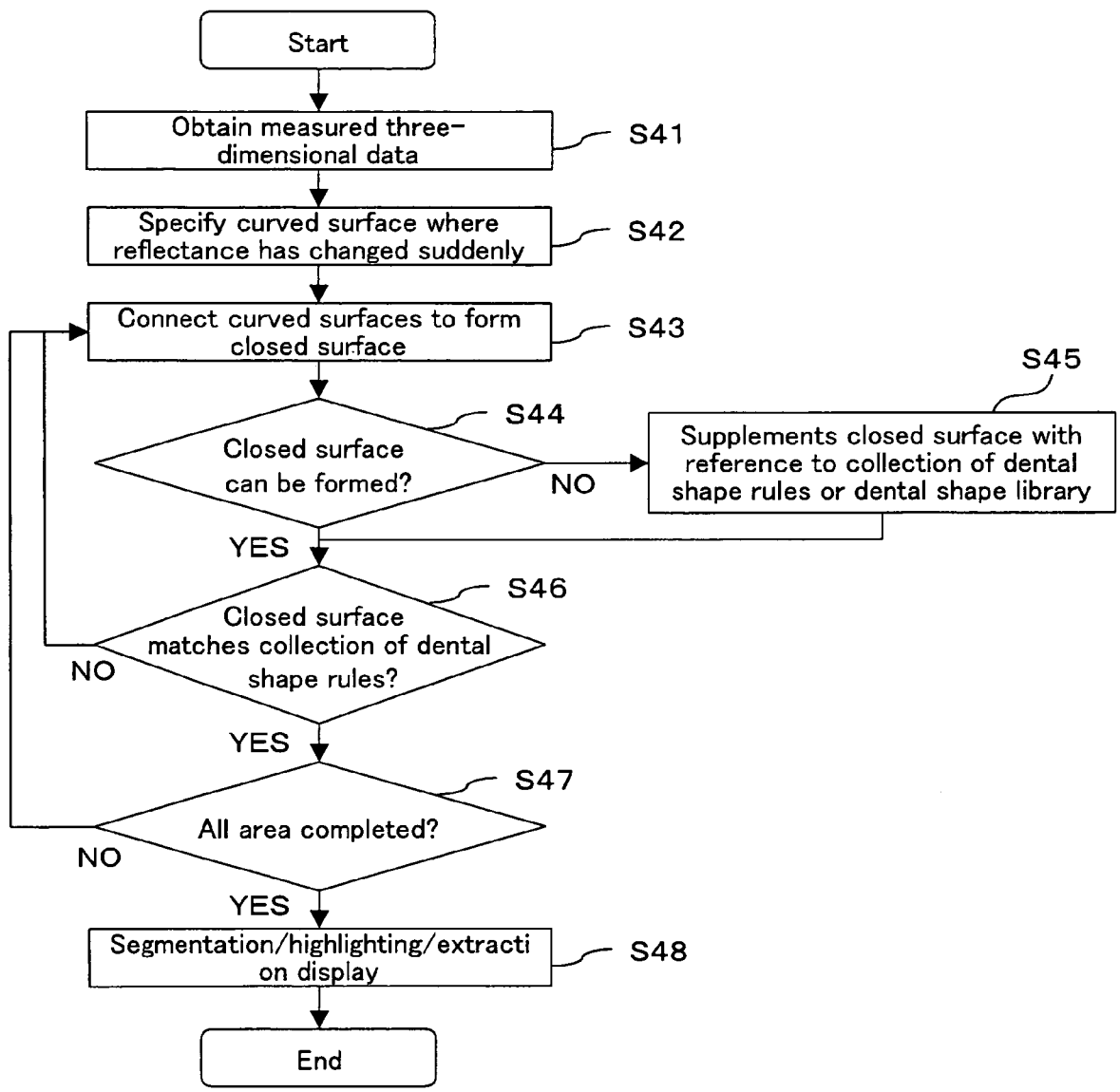
FIG. 5 is a flowchart showing an example of the processing in which the arithmetic portion displays an image of a measured object.

Next, an example of the processing performed in the case where the arithmetic portion 27b displays an image of the measured object 22 generated based on the data detected at the photodetector 41 will be described. FIG. 5 is a flowchart showing an example of the processing in which the arithmetic portion 27b displays an image of the measured object 22. As shown in FIG. 5, the arithmetic portion 27b obtains three-dimensional data representing the shape of the measured object 22 from the recording portion 27c (Step S41). The three-dimensional data may be represented, for example, by the values representing the reflection intensity on the respective coordinates.

The arithmetic portion 27b extracts curved surfaces where the reflection intensity has changed suddenly from the obtained three-dimensional data (Step S42). The arithmetic portion 27b connects the extracted curved surfaces to form a closed surface (Step S43). If a closed surface cannot be formed (NO in Step S44), then the arithmetic portion 27b supplements a closed surface with reference to the dental shape data recorded previously in the recording portion 27c (Step S45). The dental shape data may be a collection of dental shape rules and a dental shape library, for example. FIG. 6 shows an example of the data structure of a collection of dental shape rules. In the example shown in FIG. 6, the data sets representing the area, the thickness, the shape and the reflectance (relative value) are recorded for each of the enamel layer, the dentine layer, the cementum layer and the alveolar bone.

FIG. 7 shows an example of the shapes represented by the data contained in a dental shape library. In FIG. 7, the shapes represented by the data sets of the enamel layer, the dentine layer, the cementum layer and the alveolar bone, respectively, are shown.

For example, the arithmetic portion 27b can extract a tomographic image of a certain closed surface from three-dimensional data representing an image of the measured object 22, calculate the cross-correlation between this tomographic image and the shape represented by the data contained in the library, and determine which area of the tooth corresponds to the closed surface based on whether the cross-correlation reaches a certain level. For example, the above-described cross-correlation may be an integration containing the product of a function wherein the average value of both shape data sets is zero.

The dental shapes represented by the dental shape data are not limited to the examples shown in FIGS. 6 and 7. For example, it is also possible to record the dental shape data representing the shape of a prosthetic appliance, a lesion, a filling, etc. in the recording portion 27c.

The arithmetic portion 27b judges whether there is a match between the position, arrangement, shape, dimensions, etc. of the closed surface formed and the collection of the dental shape rules, and the dental shape library (Step S46). Thus, the area that matches the closed surface formed is extracted. As a result, a certain closed surface may be determined to be an upper part of the gum of the enamel layer, for example. The arithmetic portion 27b can determine which area of the tooth matches the closed surface by carrying out pattern matching between the dental shape data and the closed surface. In the case where the data representing the shape of a prosthetic appliance, a lesion, a filling, etc. is contained in the dental shape data, the closed surface representing the area representing the lesion, the prosthetic appliance, or the filling can be extracted in the same manner.

If the closed surface does not match any area (NO in Step S46), then the arithmetic portion 27b forms a closed surface again (Step S43). If the area of the closed surface is determined (YES in Step S46), then the arithmetic portion 27b judges whether the closed surface has been extracted for all the areas in the measured object 22 (Step S47).

If the closed surface has been extracted for all the areas (YES in Step S47), then the arithmetic portion 27b outputs each of the areas to the display portion 27a in such a manner that it can be distinguished visually from other areas (Step S48). For example, the areas of the image of the measured object 22 can be segmented for display. Such segmentation can be performed, for example, by displaying each of the areas in a different color. Besides the segmentation, it is also possible to highlight or extract only a specific area for display. Such segmentation, highlighting or extraction for displaying the measured object 22 makes it easy for an operator looking at the displayed image to carry out a diagnosis.

Example of the Structure of the Probe Unit 200

Figure 8A:
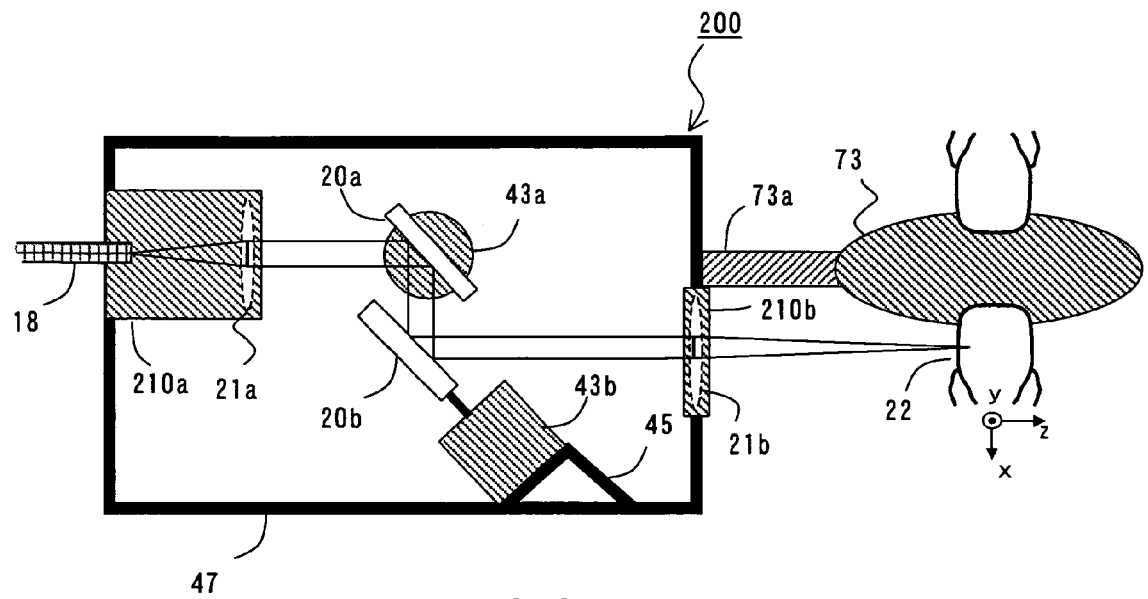
FIG. 8A is a cross-sectional view showing the internal structure of a probe unit 200 shown in FIG. 1.

Next, the structure of the probe unit 200 will be described. FIG. 8A is a cross-sectional view showing the internal structure of the probe unit 200 shown in FIG. 1. The probe unit 200 includes lenses 21a and 21b, lens holders 210a and 210b, galvano mirrors 20a and 20b, galvano mirror driving motors 43a and 43b that are provided inside a housing 47, as well as a mouthpiece 73 and a mouthpiece holder 73a that are provided outside the housing 47.

The lens holders 210a and 201b fix the lenses 21a and 21b to the housing 47 inside the probe unit 200. The galvano mirror driving motor 43a rotates the galvano mirror 20a about the y-axis direction, and the galvano mirror driving motor 43b rotates the galvano mirror 20b about a direction parallel to the x-y plane. The galvano mirror driving motor 43b is fixed to the housing 47 with a spacer 45, and the galvano mirror driving motor 43a is fixed to the housing 47 with another spacer (not shown).

The operations of the galvano mirror driving motors 43a and 43b may be controlled, for example, by a signal from the calculating machine 27 shown in FIG. 1. For example, the calculating machine 27 can operate the galvano mirror driving motors 43a and 43b so that galvano mirrors 20a and 20b rotate within a predetermined angle range.

In addition, the probe unit 200 is connected to the OCT unit 100 with the optical fiber 18. The measuring light 28 entering the probe unit 200 via the optical fiber 18 passes through the lens 21a, is reflected at the galvano mirrors 20a and 20b, passes through the lens 21b, and is focused on the measured object 22. The reflected component of the measuring light 28 reflected at the measured object 22 passes through the lens 21b again, is reflected at the galvano mirrors 20b and 20a, passes through the lens 21a, and is guided to the optical fiber 18.

The calculating machine 27 can perform scanning in the y-axis direction on the measured object 22 for the measuring light 28 reflected at the galvano mirror 20b and traveling onto the measured object 22, for example, by stopping the galvano mirror 20a and rotating the galvano mirror 20b about a direction parallel to the z-y plane by a fixed angle. Alternatively, the calculating machine 27 can perform scanning in the x-axis direction of the measured object 22 for the measuring light 28 reflected at the galvano mirror 20a, thereafter reflected at the galvano mirror 20b and traveling onto the measured object 22, for example, by stopping the galvano mirror 20b and rotating the galvano mirror 20a about the y-axis direction by a fixed angle.

In this embodiment, the probe unit 200 and the OCT unit 100, which includes an interferometer such as the fiber coupler 19, are connected with a single optical fiber 18. Accordingly, the probe unit 200 can move flexibly in accordance with the position and the shape of the measured object 22. Furthermore, the probe unit 200 contains a means for scanning in the x-axis direction and the y-axis direction. Accordingly, it is possible to obtain three-dimensional information, including the depth direction (z-axis direction), of the measured object 22. Of the three-dimensional information, information of one dimension is obtained by electric/optical scanning of the light source wavelength, and information of the remaining two dimensions is obtained by mechanical scanning with the probe unit 200. This makes it possible to perform measurement free from the constraint of the position of the OCT unit 100, and also to obtain the three-dimensional information of the measured object. This provides an exceptional advantage in the field of dentistry.

In addition to the method in which the galvano mirrors 20a and 20b are driven, a method using a cylindrical lens, methods in which a lens, an optical fiber or the measured object 22 is driven, a method in which the operator moves the probe unit 200, or the like, which will be described later, can be used as the method for scanning in the y-axis direction and in the x-axis direction. In addition, the method in which the galvano mirrors 20a and 20b are driven is not limited to cases using the galvano mirror driving motors 43a and 43b described above.

Hereinafter, the method in which a lens is driven will be described as a modification of the method for scanning in the y-axis direction.

FIG. 9 is a conceptual diagram for illustrating an example of the method in which a lens is driven. A linear actuator 31 is connected to one end of the lens 30, and the other end of the lens 30 is fixed to the apparatus. The lens 30 is driven by the linear actuator 31 in the z direction, thereby causing a circular-arc reciprocating motion around a rotation shaft 32. As a result of the circular-arc reciprocating motion of the lens 30, the optical axis of the lens 30 moves within the z-y plane, and thereby the measured object is scanned in the y direction.

In order to obtain a three-dimensional structure of the measured object 22, it is necessary to perform scanning in the x-axis direction, in addition to scanning in the z-axis direction by the wavelength sweeping of the light source 15 and mechanical scanning in the y-axis direction. The scanning in the x-axis direction can be performed by driving the galvano mirror 20 also in the x-axis direction as in the scanning in the y-axis direction. Methods that are similar to the examples of the methods for scanning in the y-axis direction also can be used for the scanning in the x-axis direction. The scanning in the y-axis and the x-axis direction can be performed by combining any suitable ones of the above-described examples of the methods for scanning in the y-axis direction.

In addition, a configuration in which the probe unit 200 is provided with a bi-directional scanning means, as the example shown in FIG. 8A, is applicable not only to FD-OCT apparatuses, but also to conventional OCT apparatuses.

Example of the Configuration of the Mouthpiece

Figure 8B:
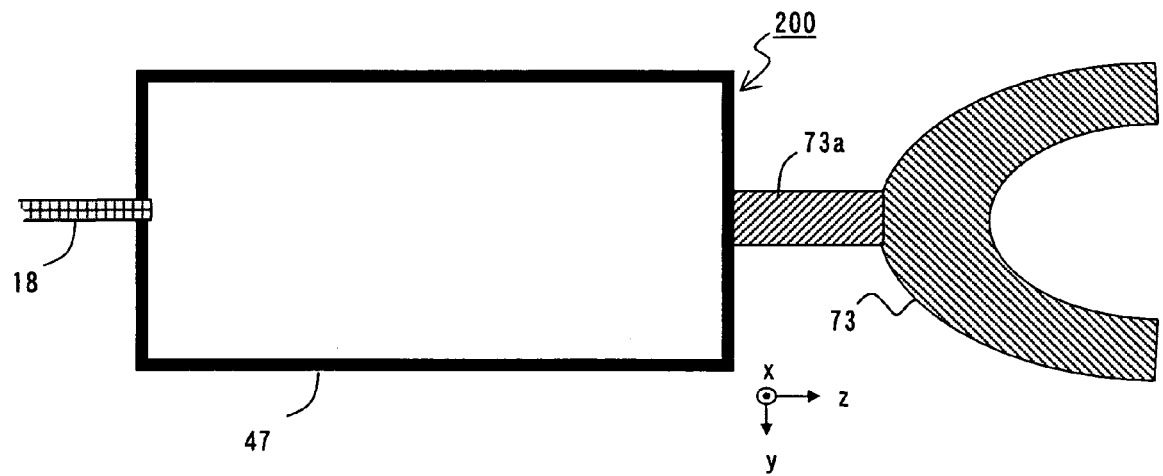
FIG. 8B is a plane view of the probe unit 200, as viewed from the x-axis direction.

Next, the mouthpiece 73 and the mouthpiece holder 73a that are provided outside the probe unit 200 shown in FIG. 8A will be described. FIG. 8B is a plane view of the probe unit 200, as viewed from the x-axis direction. As shown in FIGS. 8A and B, the mouthpiece holder 73a is fixed to the housing 47 of the probe unit 200. The mouthpiece 73 is provided at the tip of the mouthpiece holder 73a. The plane of the mouthpiece 73 viewed from the x-axis direction, for example, is horseshoe-shaped, matching the shape of the dentition of a human being. That is, the mouthpiece 73 has a curved shape adapted to match the shape of the dentition. In addition, the mouthpiece preferably is formed using an impression (mold) of the dentition of a specific patient.

In the case where the measured object 22 is a tooth of a living body, the relative position between the tooth, which is the measured object 22, of a measured person and the probe unit 200 is fixed by the measured person biting on the mouthpiece 73 so that his/her dentition follows the shape of the mouthpiece 73. In a state where the three-dimensional positional relationship between the probe unit 200 and the tooth of the measured person is fixed in this way, the measuring light 28 is radiated from the probe unit 200 to the tooth, which is the measured object 22. Thus, the measured object 22 is positioned with respect to the measuring light 28 accurately.

Accordingly, the irradiation position of the measuring light 28 flexibly can be changed in accordance with the shape of the measured object 22 by moving the probe unit 200, and the relative position between the probe unit 200 and the measured object 22 can be fixed by the measured person biting on the mouthpiece 73 with his/her teeth, which is the measured object 22.

It is also preferable that the mouthpiece 73 is formed of an elastic material. Then, when the mouthpiece 73 is bitten with the teeth, the teeth bite into the mouthpiece 73, so that the relative position between the teeth, which is the measured object 22, of the measured person and the probe unit 200 is fixed in a stable manner.

It should be noted that the configuration of the mouthpiece 73 and the mouthpiece holder 73a is not limited to the shape shown in FIGS. 8A and 8B. FIG. 10 shows another example of the configuration of the mouthpiece 73 and the mouthpiece holder 73a. In the example shown in FIG. 10, the area of contact between a mouthpiece 74 and a mouthpiece holder 74a differs from that in the example shown in FIG. 8B. The mouthpiece 73 shown in FIG. 8B is configured such that the apex of the curved portion is fixed to the mouthpiece holder 73a, and that the measured object 22 is the anterior teeth region. In FIG. 10, the mouthpiece 74 is configured such that the lateral side of the curved portion of the mouthpiece 74 is fixed to the mouthpiece holder 74a, and that the measured object 22 is a canine, the molar region or the like.

Figure 11A:
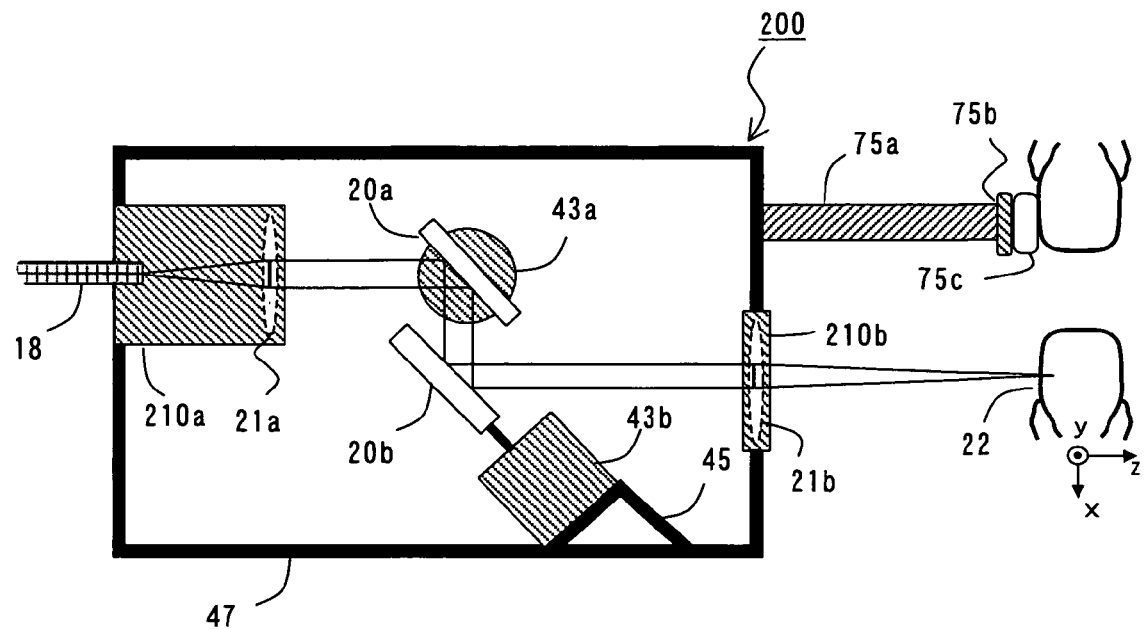
FIG. 11A is a cross-sectional view of the probe unit in the case of using a splint instead of a mouthpiece.
Figure 11B:
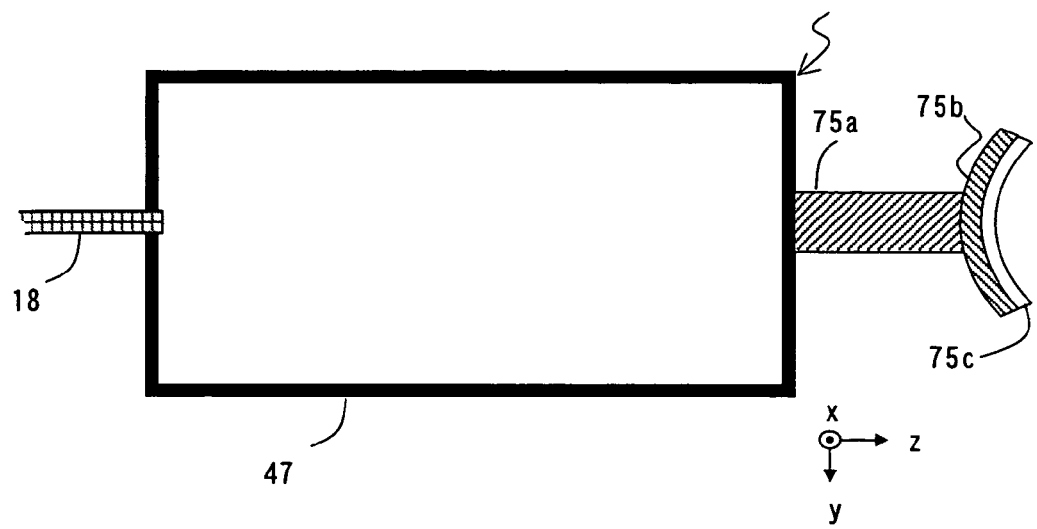
FIG. 11B is a plane view of the probe unit in FIG. 11A, as viewed from the x-axis direction.

Besides the mouthpiece, a splint and a splint holder can be used as means for fixing the probe unit 200 and the measured object 22 together. FIG. 11A is a cross-sectional view of the probe unit 20 in the case of using a splint instead of the mouthpiece. FIG. 11B is a plane view of the probe unit 200 in FIG. 11A, as viewed from the x-axis direction.

A splint holder 75a is fixed to the housing 47 in the example shown in FIGS. 11A and 11B. A splint core 75b is provided at the tip of the splint holder 75a. An adhesive member 75c is provided between the splint core 75b and the tooth. It is preferable that the adhesive member 75c is shaped to match the shape of the tooth. As the adhesive member 75c, a commercially available self-curing resin can be used, for example. It should be noted that the adhesive member 75c is not a component of the probe unit 200.

Thus, it is possible to stabilize the position and the orientation of the probe unit 200 with respect to the dentition by shaping the adhesive member 75c to match the shape of the dentition including the measured object 22. Moreover, the probe unit 200 can be arranged in the same position and the same orientation as a previous measurement relative to the measured object 22 by moving the probe unit 200 away from the measured object 22 once and bringing it close to the measured object 22 again to fit the adhesive member 75c against the dentition including the measured object 22.

For example, in such a case where a patient, who has already been measured, revisits the clinic, the orientation and the position of the probe unit 200 relative to the measured object 22 in the previous measurement can be reproduced. In remeasurement and clinical observation, it is possible to perform measurement with reproducibility, relative to the past measurement. That is, in the case of carrying out diagnosis of the change in a treated area, for example, in measurements before and after the treatment, namely, one week, one month and one year after the completion of the treatment, it is possible to perform measurement with the same position and the same orientation. This is effective not only for knowing the occurrence of a disease after the treatment, but also for providing evidence for objectively proving the absence (or presence) of mistreatment. In addition, the mouthpiece also may be shaped to match the shape of the dentition.

For example, if the measured object 22 is a tooth in an occlusal condition, as shown in FIG. 8A, the position of the probe unit 200 and the measured object 22 cannot be fixed by the measured person biting on the mouthpiece 73. In such a case, for example, the splint holder 75a and the splint core 75b as shown in FIG. 11 can be used as a fixing means.

The mouthpiece holder 73a and the splint holder 75a may be configured such that they are removable from the probe unit 200 and interchangeable. Further, by configuring the mouthpiece holder 73a and the splint holder 75a to be removable, it is possible to remove the mouthpiece holder 73a and the splint holder 75a for sterilization treatment. Further, the mouthpiece holder 73a and the splint holder 75a may be removable and disposable. A disposable cover may be attached on the mouthpiece when in use.

Example of a Mouthpiece Including a Cheek Retractor

Figure 12A:
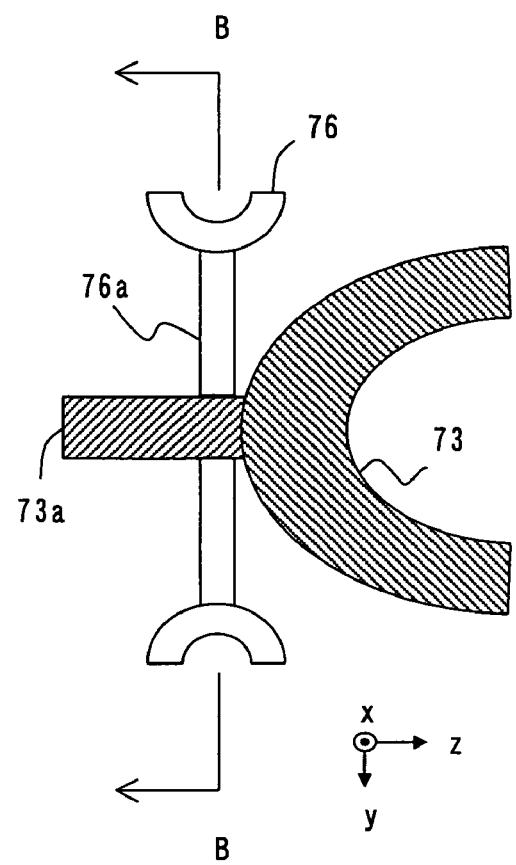
FIG. 12A is a cross-sectional view in the y-z plane of a mouthpiece and a mouthpiece holder with which a cheek retractor 76 is provided.
Figure 12B:
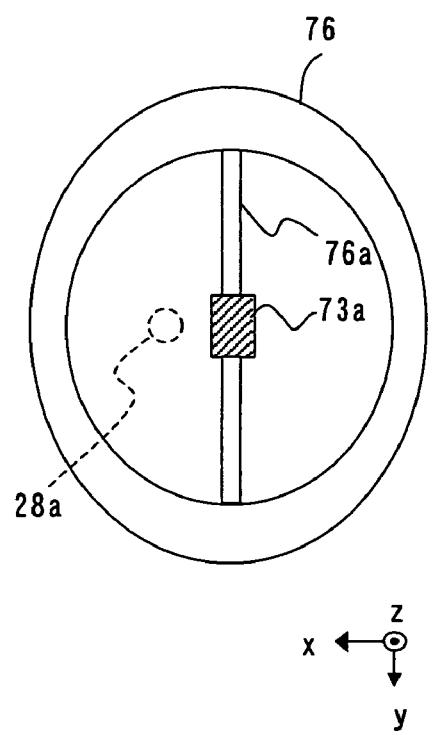
FIG. 12B is a diagram showing a cross section of the mouthpiece holder 73a and the cheek retractor 76 shown in FIG. 12A, taken along the B-B line.

The mouthpiece or the splint may be provided with a cheek retractor for preventing an obstruction such as lips from being positioned between the exit port of the measuring light 28 of the probe unit 200 and the measured object 22. FIG. 12A is a cross-sectional view in the y-z plane of the mouthpiece 73 and the mouthpiece holder 73a, with which a cheek retractor 76 is provided. FIG. 12B is a diagram showing a cross section of the mouthpiece holder 73a and the cheek retractor 76 shown in FIG. 12A, taken along the line B-B. As shown in FIGS. 12A and 12B, the cheek retractor 76 is a ring centered on mouthpiece holder 73a. The cheek retractor 76 is fixed to the mouthpiece holder 73a with a connecting portion 76a that connects the inner side of the ring to the mouthpiece holder 73a.

With the configuration shown in FIG. 12, for example, when the measured person with the tooth that is the measured object 22 bites on the mouthpiece 73, the lips of the measured person stop at the outer side of the ring of the cheek retractor 76 in this state, and do not enter the inner side of the ring of the cheek retractor 76. In other words, the mouth of the measured person will be forced open by the cheek retractor 76. Accordingly, it is possible to prevent the lips of the measured person from entering the optical path of the measuring light 28 that is located at the inner side of the ring. In FIG. 12B, a dotted circle 28a denotes a cross section of the measuring light 28 traveling in the z direction.

In addition, the configuration in which the probe unit 200 is provided with the fixing means such as a mouthpiece and a splint is applicable not only to FD-OCT apparatuses as in the above-described example, but also to conventional OCT apparatuses.

Modification of the Mouthpiece

Figure 13:
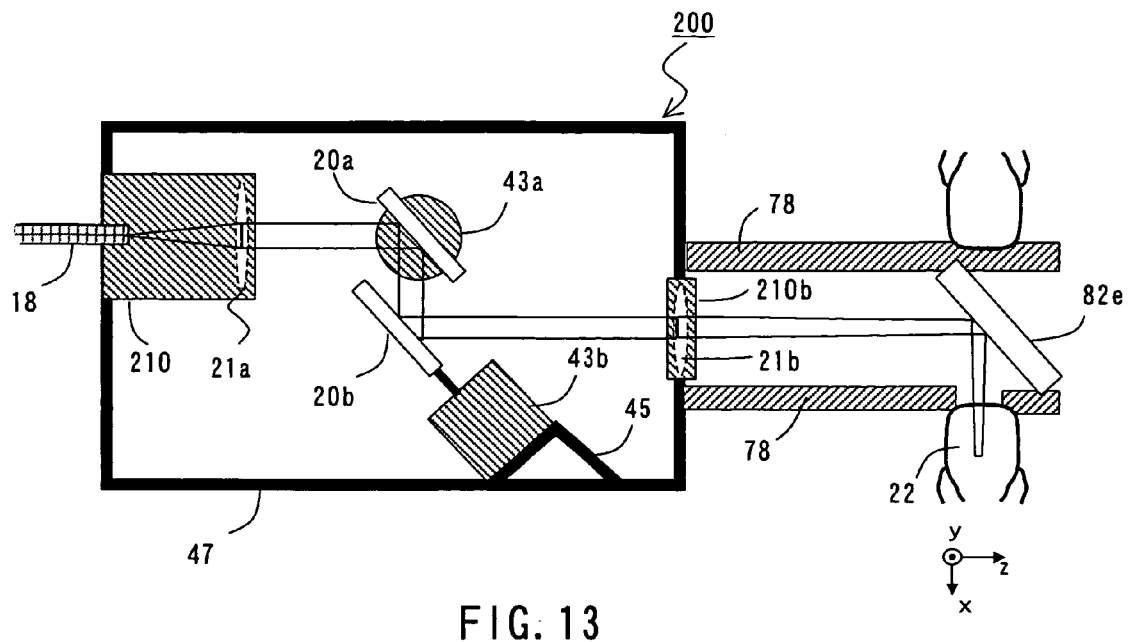
FIG. 13 is a cross-sectional view showing a modification of the mouthpiece.

FIG. 13 is a cross-sectional view showing a modification of the mouthpiece. A mouthpiece 78 shown in FIG. 13 is formed in a tubular shape so that it has a cavity inside. The mouthpiece 78 is fixed to the housing 47 of the probe unit 200 so that the measuring light 28 from the probe unit 200 can be radiated to the cavity inside the mouthpiece 78. A hole 78a for allowing passage of the measuring light 28 is formed in a side surface of the mouthpiece 78. In addition, an objective mirror 82e for guiding the measuring light 28 to the hole 78a is provided inside the mouthpiece 78.

For example, in the case where the measured object 22 is a tooth, the relative position between the measured object 22 and the probe unit 200 can be fixed by the measured person biting on the mouthpiece 78 so that the hole 78a is covered with the tooth that is the measured object 22.

Further, the measuring light 28 emitted from the probe unit 200 is reflected at the objective mirror 82e, and radiated from the hole 78a to the measured object 22 located outside the mouthpiece 78. The reflected component of the measuring light 28 reflected at the measured object 22 enters the cavity in the mouthpiece 78 from the hole 78a, and reflected at the objective mirror 82e so that it is directed into the probe unit 200.

The mouthpiece 73 shown in FIG. 8 is suitable for radiating the measuring light 28 to the labial surface of a tooth or a gum, whereas the mouthpiece 78 shown in FIG. 13 is suitable for radiating the measuring light 28 to the occlusal surface of a tooth or a gum.

Modification of the Probe Unit

Figure 14:
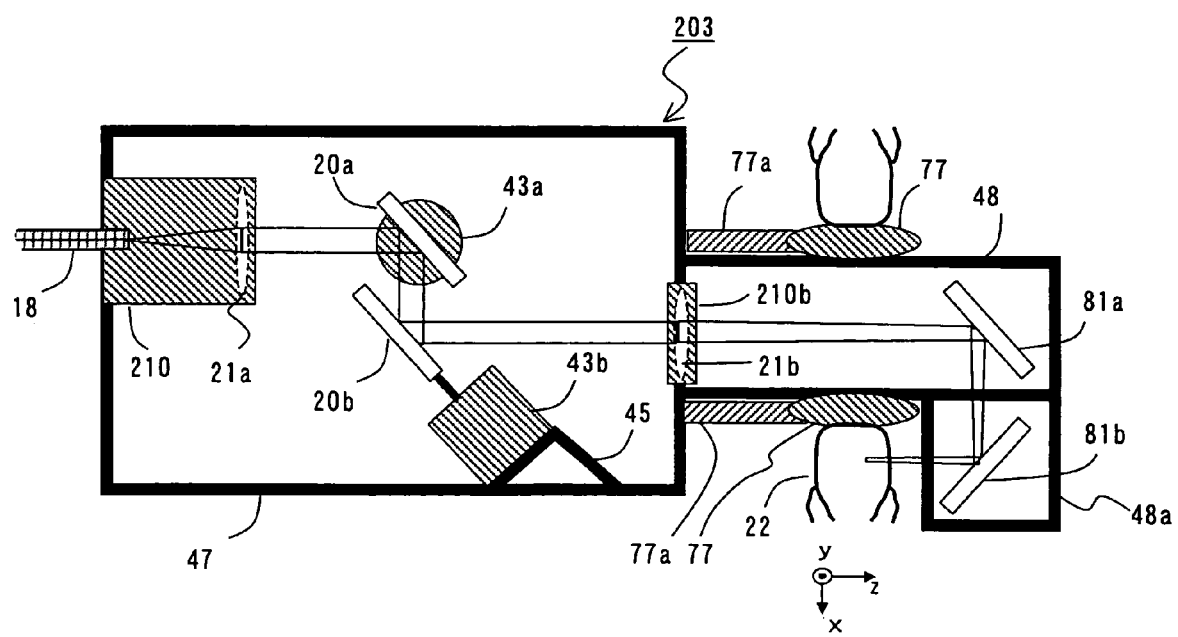
FIG. 14 is a cross-sectional view showing a modification of the probe unit according to this embodiment.

FIG. 14 is a cross-sectional view showing a modification of the probe unit according to this embodiment. A probe unit 203 shown in FIG. 14 further includes a guide 48 protruding from the housing 47. A light irradiation portion 48a having a window for allowing entrance and exit of the measuring light 28 is provided at the tip of the guide 48. The window for allowing entrance and exit of the measuring light 28 is provided on a surface of the light irradiation portion 48a on the probe unit 203 side. The guide 48 and the light irradiation portion 48a include an intermediate mirror 81a and an objective mirror 82a, respectively, for changing the traveling direction of the measuring light 28.

The measuring light 28 emitted from the housing 47 through the lens 21b is reflected at the intermediate mirror 81a and the objective mirror 82a, thus changes its traveling direction by 180 degrees, and exits from the window of the light irradiation portion 48a. With the configuration of the probe unit 203 shown in FIG. 14, it is possible to perform measurement, for example, for a measured object 22 that is located at an intricate position such as the lingual surface of a tooth.

In addition, a mouthpiece 77 and a mouthpiece holder 77a are provided on the upper surface and the lower surface of the guide 48, respectively, and they can be bitten by a measured person with a tooth that is the measured object 22, so that the guide 48 is sandwiched between the upper and lower teeth. Thus, the relative position between the probe unit 203 and the tooth, which is the measured object 22, is fixed.

Other Modifications of the Mouthpiece

It is also possible to adopt a configuration in which the probe unit is fixed to the mouthpiece 73 or the splint core 75b, and can move along a guide formed to follow the dentition. For example, it is also preferable to adopt a structure in which the mouthpiece holder 73a and the probe unit 200 slide following the shape of the mouthpiece 73 in FIG. 8B.

Figure 15A:
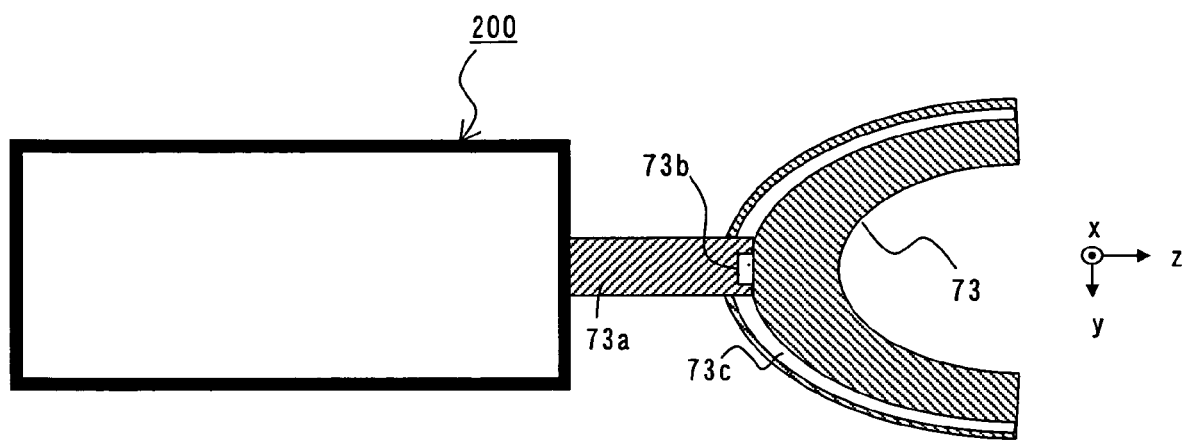
FIG. 15A is a diagram showing an example of the structure in which the mouthpiece holder and the probe unit slide following the shape of the mouthpiece.
Figure 15B:
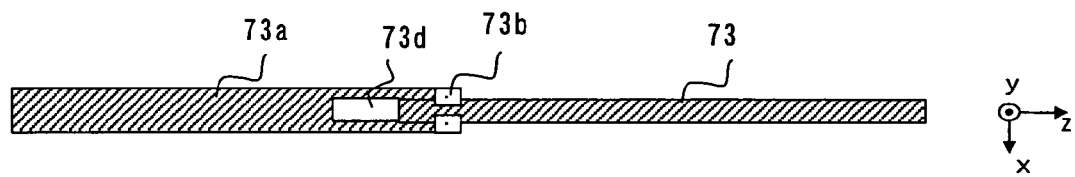
FIG. 15B is a cross-sectional view in the x-y plane of the mouthpiece holder and mouthpiece shown in FIG. 15A.

FIG. 15A is a diagram showing an example of the structure in which the mouthpiece holder 73a and the probe unit 200 slide following the shape of the mouthpiece 73. FIG. 15B is a cross-sectional view in the x-y plane of the mouthpiece holder 73a and mouthpiece 73 shown in FIG. 15A.

A guide groove 73c is formed in the mouthpiece 73 shown in FIGS. 15A and 15B. The guide groove 73c is formed in a U-shape so that it follows the dentition of the teeth biting on the mouthpiece 73. The mouthpiece holder 73a is fixed to the probe unit 200. The tip of the mouthpiece holder 73a is divided into an upper section and a lower section, and has a shape that can sandwich the mouthpiece 73 between the upper section and the lower section. A claw 73b is provided at each of the upper and lower sections of the tip of the mouthpiece holder 73a. The claw 73b is dimensioned so that it can fit into the guide groove 73c of the mouthpiece 73. Accordingly, the mouthpiece 73 can be fixed to the mouthpiece holder 73a with the claw 73b.

The mouthpiece holder 73a is configured such that a cavity 73d is formed therein when the mouthpiece 73 is sandwiched at its tip. When force is applied to the cavity 73d portion of the mouthpiece holder 73a from the upper and lower sides, the force being exerted by the claw 73b to sandwich the mouthpiece 73 is reduced. For example, fixation of the mouthpiece holder 73a to the mouthpiece 73 is eased by an operator pushing the cavity 73d portion of the mouthpiece 73 with his/her finger. Once the fixation has been eased, the operator can move the mouthpiece holder 73a along the guide groove 73c. The claw 73b fits into the guide groove 73c deeply when the operator releases his/her finger, so that the mouthpiece 73 is fixed to the mouthpiece holder 73a.

With the above-described configuration, the mouthpiece holder 73a and the probe unit 200 can slide along the guide groove 73c of the mouthpiece 73. As a result, it is possible to perform measurement for a plurality of teeth in the dentition that bites on the mouthpiece 73.

Figure 16:
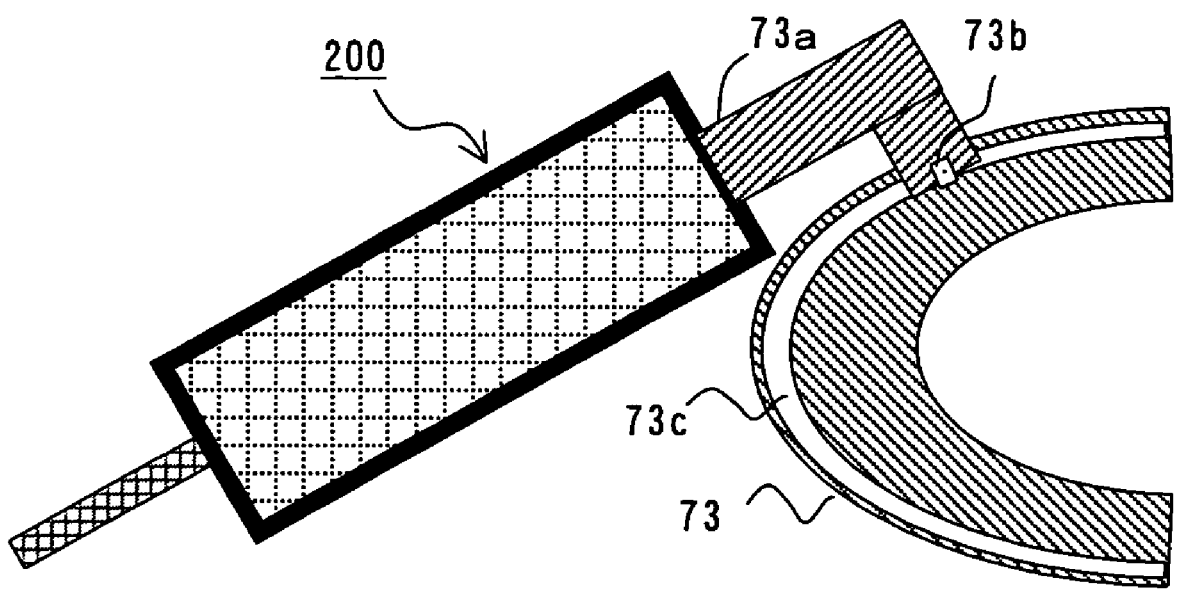
FIG. 16 is a diagram showing an example of the shape of a mouthpiece holder bent at a right angle.

As shown in FIG. 16, the mouthpiece holder 73a also may be shaped so that it is bent at a right angle. In this case, although not shown, it is preferable to provide a guide 48 having a mirror 81a as shown in FIG. 14 in the probe unit 200. Thus, the optical axis of the measuring light emitted from the probe unit 200 can be bent by 90 degrees. Consequently, it is also possible to insert the probe unit 200 from an opening of the oral cavity, and radiate the measuring light onto the molar area at a slant angle.

Example Using a Spacer as the Fixing Member

Figure 17A:
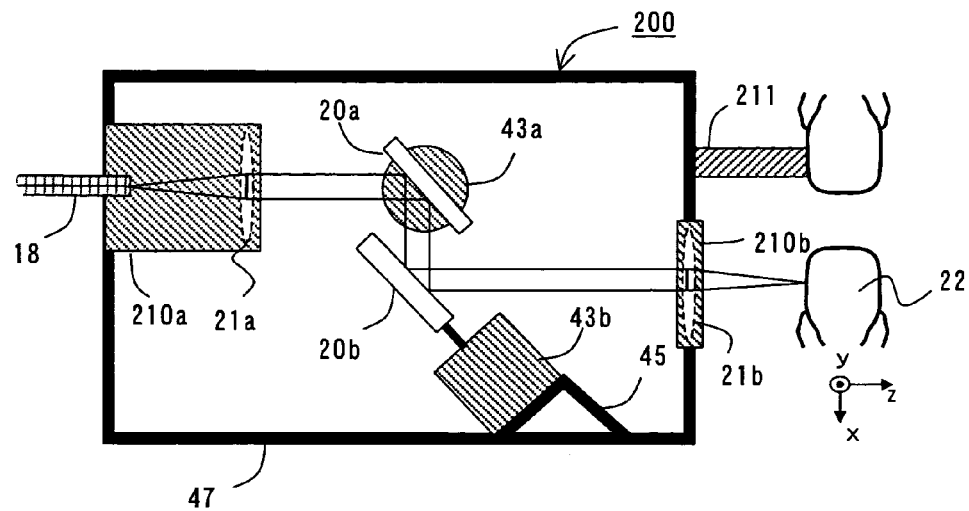
FIG. 17A is a cross-sectional view of a probe unit in the case of using a spacer as a fixing member.

Besides the mouthpiece or the splint, it is possible, for example, to use a spacer as the fixing member for fixing the probe unit 200 to the measured object. FIG. 17A is a cross-sectional view of the probe unit 200 in the case of using a spacer as the fixing member. In the example shown in FIG. 17A, a spacer 211 is fixed to the probe unit 200. A surface to be brought into contact with the measured object 22 is formed at the tip of the spacer 211. The length of the spacer 211 is determined in accordance with the focal length of the lens 21b. That is, the length of the spacer 211 is determined so that the focal point of the measuring light 28 focused by the lens 21b is located on the surface or the inside of the measured object 22 when the spacer 211 is in contact with the measured object 22.

If the above-described mouthpiece is used as the fixing member, fixation is achieved in a state in which the mouthpiece is bitten with the upper and lower teeth, which is the measured object 22, so that stable fixation can be achieved. However, once fixation has been achieved, it will be troublesome to change the measuring position of the probe unit 200. On the other hand, in the case of using the spacer 211 as the fixing member, the position of the probe unit 200 is fixed with the spacer 211 in contact with the measured object 22, which makes it easy to change the measuring position of the probe unit 200. That is, the operator can manipulate the measuring position of the probe unit 200 freely, and can fix the measuring position during measurement.

Figure 17B:
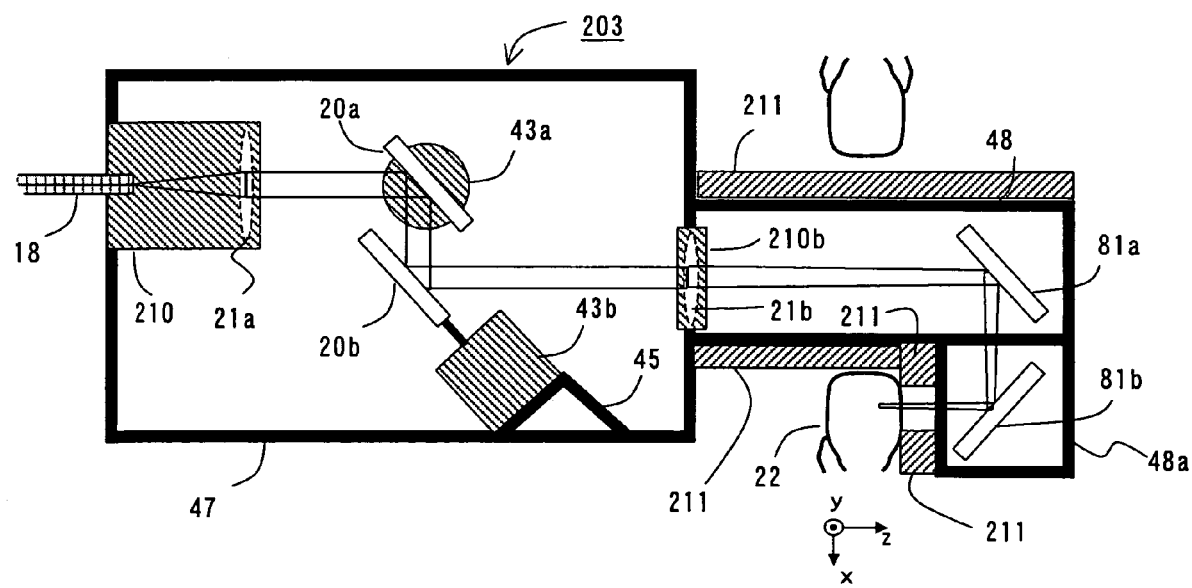
FIG. 17B is a cross-sectional view showing a modification of the probe unit including a spacer.

FIG. 17B is a cross-sectional view showing a modification of the probe unit including the spacer. The probe unit 203 shown in FIG. 17B is the same as the probe unit 203 shown in FIG. 14. The probe unit 203 shown in FIG. 17B is provided with the spacer 211 instead of the mouthpiece holder 77a and the mouthpiece 77. By bringing the measured object 22 into contact with a part of the spacer 211, the position and orientation of the probe unit 203 relative to the measured object 22 can be fixed.

Figure 18A:
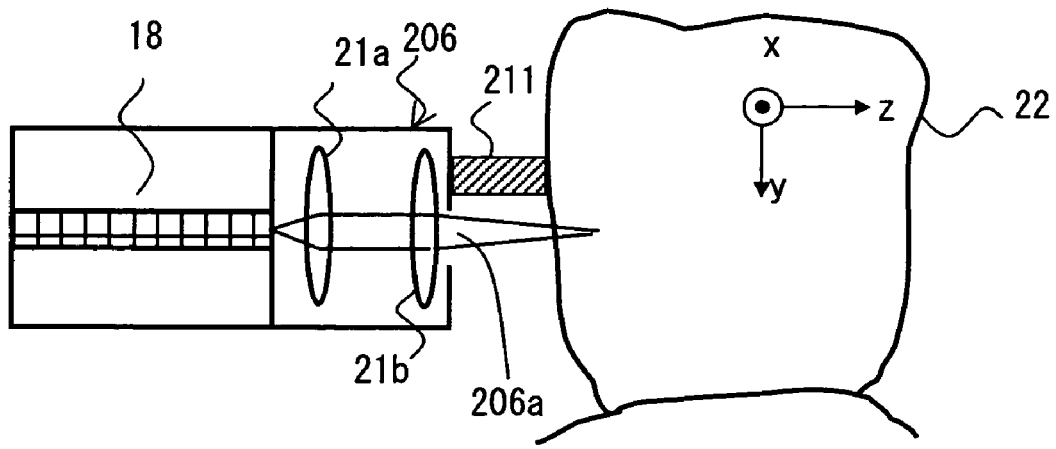
FIGS. 18A and B are diagrams showing modifications of the probe unit including a spacer.
Figure 18B:
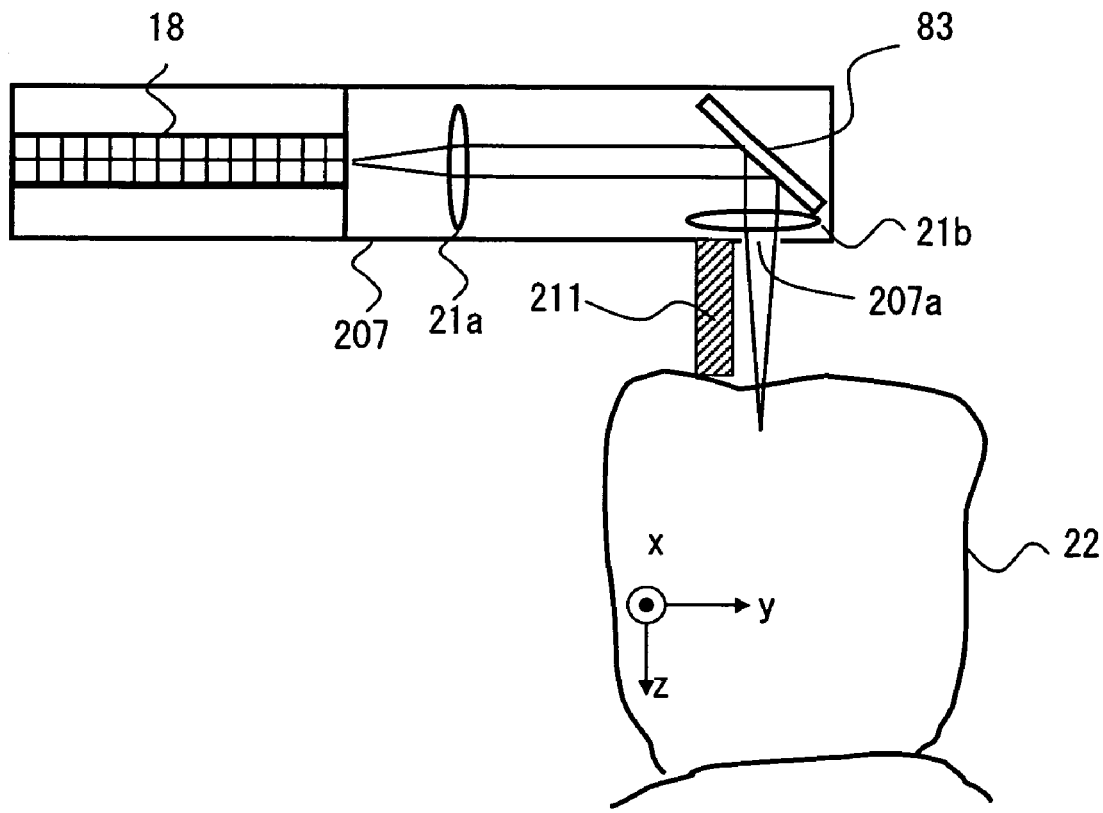

FIGS. 18A and 18B are diagrams showing modifications of the probe unit including the spacer. A probe unit 206 shown in FIG. 18A includes lenses 21a and 21b for guiding the measuring light from the optical fiber 18 to the measured object 22. In addition, the probe unit 206 is provided with a window 206a for emitting the measuring light 28. The spacer 211 is fixed to the side of the probe unit 206 on which the window 206a is provided.

In the probe unit 206 shown in FIG. 18A, the measuring light 28 emitted from the fiber 18 is collimated by the lens 21a, focused by the lens 21b, and guided to the measured object 22. The length of the spacer 211 in the direction of the optical axis of the measuring light 28 is determined in accordance with the focal length of the lens 21b. That is, the length of the spacer 211 is determined so that the focal point of the lens 21b is located inside the measured object 22 when the spacer 211 is in contact with the measured object 22.

The probe unit 206 shown in FIG. 18A does not include a means for scanning the measuring light in the x-axis direction or the y-axis direction. The operator can perform scanning by moving the probe unit 206 in the x-axis direction or y-axis direction while holding it in his/her hand. In this case, by moving the probe unit 206 with the spacer 211 in contact with the measured object 22, the operator can perform scanning while a constant distance is maintained between the measured object 22 and the probe unit 206. This makes it possible to perform measurement with high resolution and a high degree of reach (the maximum depth at which the measuring light can be caused to reach and the reflected light can be captured) with a type of the probe unit that is placed over the measured object 22 freely by the operator in a hand-held manner.

A probe unit 207 shown in FIG. 18B includes a mirror 83 that changes the direction of the optical axes of the lenses 21a and 21b and the measuring light 28 by 90 degrees. The probe unit 207 is provided with a window 207a for emitting measuring light 28 whose optical axis has been altered by the mirror 83. The spacer 211 is fixed to the surface of the probe unit 207 on which the window 207a is formed.

In the probe unit 207 shown in FIG. 18B, the measuring light 28 emitted from the fiber 18 is collimated with the lens 21a, and is reflected at the mirror 83. Thereafter, the measuring light 28 is focused by the lens 21b, and guided to the measured object 22. The length of the spacer 211 is determined so that the focal point of the lens 21b is located inside the measured object 22 when the spacer 211 is in contact with the measured object 22.

Example of a Probe Unit Including a Rotating Member

Figure 19:
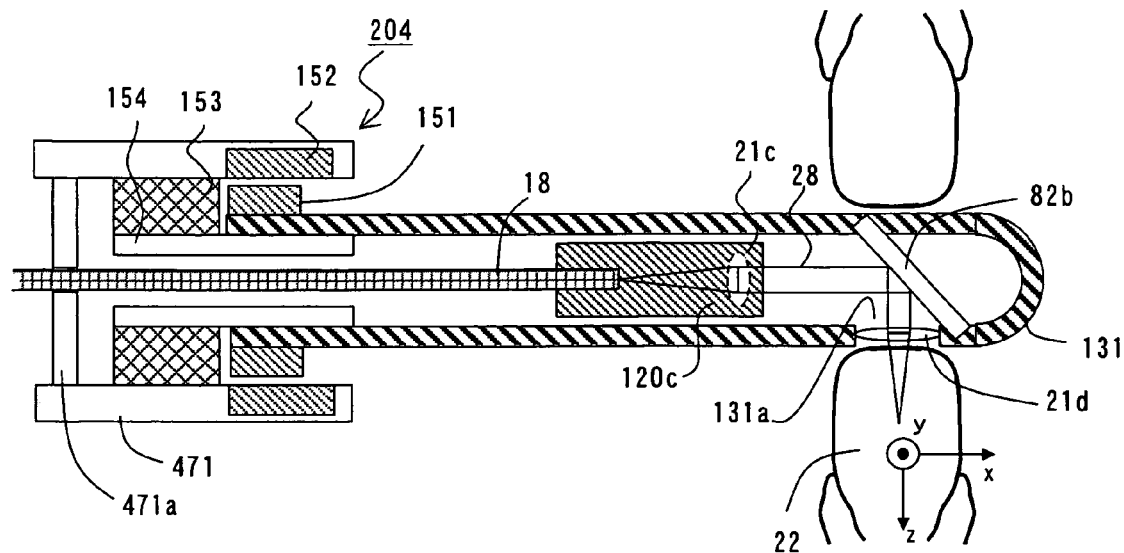
FIG. 19 is a cross-sectional view in the x-y plane showing a modification of the probe unit.

FIG. 19 is a cross-sectional view in the x-y plane, showing another modification of the probe unit according to this embodiment. A housing 471 of a probe unit 204 shown in FIG. 19 is formed into a cylindrical shape having a circular cross section in the y-z plane. A rotating member 131 is attached to the probe unit 204.

The rotating member 131 also has a cylindrical shape having a circular cross section in the y-z plane. The tip portion of the rotating member 131 is covered by a dome-like shape. A cylindrical rotating member holder 154 is provided along the inner diameter of the rotating member 131 at the end on the housing side. A portion of the rotating member holder 154 protrudes from the inner side of the rotating member 131, and a bearing 153 is provided between this protruding portion and the housing 471. Thus, the rotating member 131 can rotate about the direction of the center axis of the cylindrical shape as its rotation axis.

A motor rotor 151 is provided along the outer diameter of the housing side end of the rotating member 131. A motor stator 152 is embedded in a portion of the housing 471 that corresponds to the motor rotor 151 along the internal diameter of the housing 471. The motor rotor 151 and the motor stator 152 serve as the driving portion that rotates the rotating member 131.

The optical fiber 18 held by an optical fiber holding portion 471a of the housing 471 is guided to the inside of the rotating member 131 in the direction of the rotation axis of the rotating member. A lens 21c that collimates the measuring light 28 emitted from the optical fiber 18 into parallel light is provided at the tip of the optical fiber 18. The lens 21c is fixed to the inside of the rotating member 131 by a lens holder 210c.

Further, an objective mirror 82b is provided inside of the rotating member 131. The objective mirror 82 changes the direction of the optical path of the measuring light 28 emitted from the optical fiber 18 from the direction of the rotation axis of the rotating member 131 to a direction forming a fixed angle with the rotation axis.

An irradiation port 131a for radiating the measuring light 28 whose optical path direction has been changed by the objective mirror 82b from the inside of the rotating member 131 to the outside thereof is formed on a side surface of the rotating member 131. A lens 21d is provided at the irradiation port 131a.

With the above-described configuration, the measuring light 28 emitted from the optical fiber 18 and traveling in the direction of the rotation axis of the rotating member 131 is reflected at the objective mirror 82b, and changes its traveling direction to a direction forming a fixed angle with the direction of the rotation axis. The measuring light 28 that has changed its traveling direction emits the rotating member 131 through the lens 21d at the irradiation port 131a, and is focused on the measured object 22.

Further, the reflected component of the measuring light 28 reflected at the measured object 22 enters into the rotating member 131 from the irradiation port 131a through the lens 21d. The reflected component of the measuring light 28 that has entered the rotating member 131 from the irradiation port 131a is reflected at the objective mirror 82b, and changes its traveling direction to the direction of the rotation axis of the rotating member 131. The reflected component of the measuring light 28 that changed the traveling direction is focused by the lens 21*c*, enters the optical fiber 18, and is guided to the OCT unit 100.

When the rotating member 131 is rotated by the motor rotor 151 and the motor stator 152, the measuring light 28 radiated from the irradiation port 131*a* moves according to the direction of that rotation. As a result, the measuring light 28 is scanned in the y-axis direction of the measured object 22.

Here, an actuator that rotates the objective mirror 82*b* about the y-axis direction as the rotation axis may be provided in the rotation member 131, for example. Rotating the objective mirror 82*b* makes it possible to change the angle between the optical axis of the measuring light 28 traveling from the objective mirror 82*b* to the measured object 22 and the rotation axis of the rotating member 131. By rotating the objective mirror 82*b* about the y-axis direction as the rotation axis by the above-described actuator, the measuring light 28 can be scanned in the x-axis direction in the measured object 22.

It should be noted that the means for scanning in the x-axis direction is not limited to the above-described method. For example, the rotating member 131 may include an actuator that translates the objective mirror 82*b* or the lens 21*c* in the direction of the rotation axis of the rotating member 131.

With the probe unit 204 shown in FIG. 19, even if the measured object 22 is located in a narrow area such as tissue in the stomatognathic region, the measured object 22 can be measured using the rotating member 131.

Modification of the Rotating Member

Figure 20:
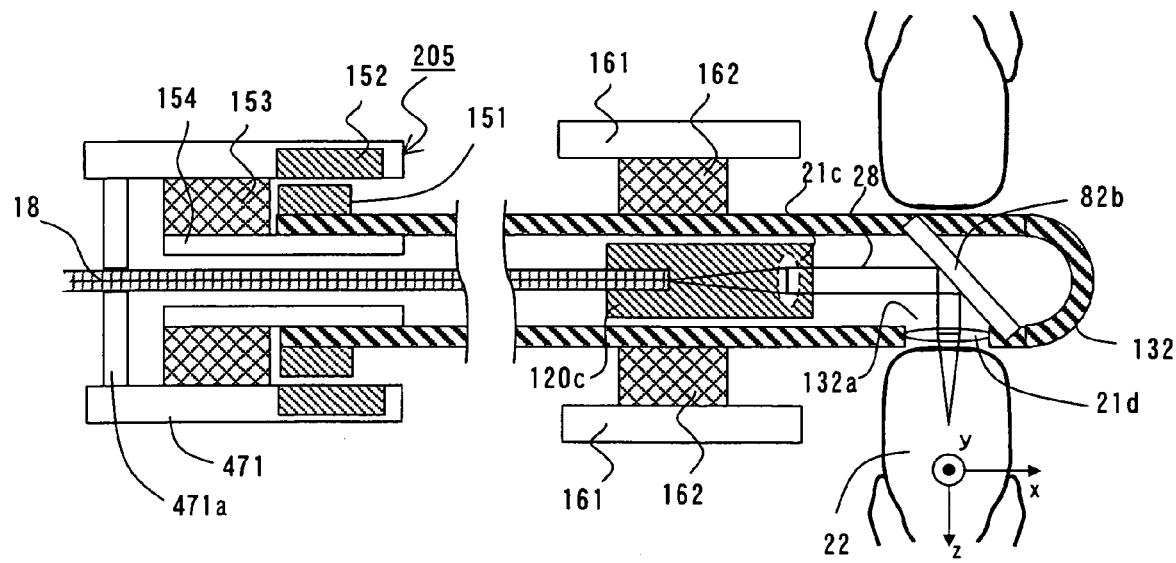
FIG. 20 is a cross-sectional view showing a modification of a rotating member.

FIG. 20 is a cross-sectional view showing a modification of the rotating member. A rotating member 132 shown in FIG. 20 is formed of a flexible material. Accordingly, the rotation shaft of the rotating member 132 can be bent so that the direction of irradiation of the measuring light 28 can be adjusted. Further, it is preferable that the length of the rotating member 132 in the direction of the rotation axis is longer than that of the rotating member 131 shown in FIG. 19.

A cylindrical sleeve 161 covering the outer periphery of the rotating member 132 is provided near the irradiation port 132*a* of the rotating member 132. A bearing 162 is provided between the sleeve 161 and the rotating member 132. Thus, even if the rotating member 132 rotates, that rotation will not be transmitted to the sleeve 161. Accordingly, fixing the sleeve 161 allows the rotating member 132 to rotate with its bending state and position maintained. As a result, it is possible to measure the measured object 22 in a state in which the relative position between the rotating member 132 and the measured object 22 is fixed.

For example, the measured object 22 can be measured in a state in which the operator holds the rotating member 132 in a suitable position while holding the sleeve 161 in his/her hand. Further, the measured object 22 can be measured in a state in which the sleeve 161 is fixed to the tip of a multi-articulated arm fixed to a stationary stage or pole, or a treatment table.

With the rotating member 132 shown in FIG. 20, it is possible to change the direction and the position of radiating the measuring light 28 flexibly in accordance with an area to be measured of the measured object 22, and fix the relative position between the rotating member 132 and the measured object 22 during measurement. Accordingly, the probe unit 205 including the rotating member 132 according to the present modification may be utilized effectively in the case where the measured object 22 is an object having a complex shape, such as tissue in the stomatognathic region.

Modification of the Sleeve

Figure 21:
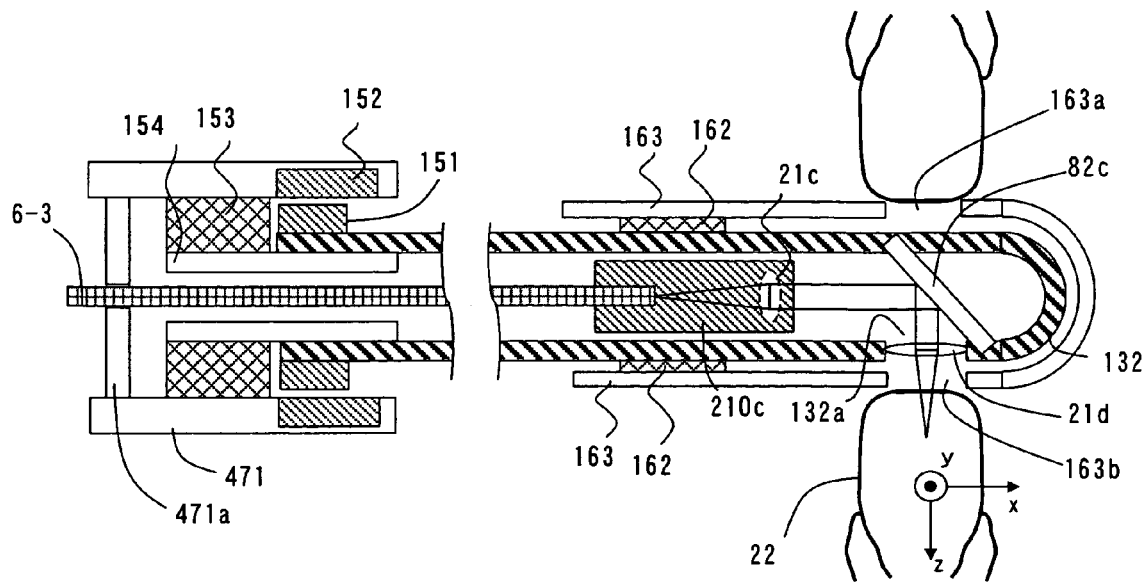
FIG. 21 is a cross-sectional view showing a modification of a sleeve.

FIG. 21 is a cross-sectional view showing a modification of the sleeve. A sleeve 163 shown in FIG. 21 is provided at the outer periphery of the rotating member 132 so that the irradiation port 132*a* and the tip of the rotating member 132 are enclosed entirely. The sleeve 163 is a cylinder covering the outer periphery of the rotating member 132, and its tip is closed in a dome-like shape. A bearing 162 is provided between the sleeve 163 and the rotating member 132. Accordingly, even if the rotating member 132 rotates, the sleeve 163 will not rotate in conjunction with this rotation.

Further, two windows 163*a* and 163*b* for allowing passage of the measuring light 28 are formed in positions opposing each other in an area of the sleeve 163 that corresponds to the irradiation port 132*a* of the rotating member 132 on a side surface of the sleeve 163. By bringing the measured object 22 into contact with the sleeve 163 so that it covers the window 163*a* or the window 163*b*, the relative positional relationship between the measured object 22 and the rotating member 132 is fixed.

For example, in the case where the measured object 22 is a tooth or a jaw bank (a gum area in a state in which the teeth have been taken out) in the oral cavity of a measured person, the relative position between the rotating member 132 and the measured object 22 can be fixed by the measured person biting on the sleeve 163 with the upper and lower dentitions or the jaw banks so that the windows 163*a* and 163*b* are covered therewith. At that time, the rotating member 132 can rotate in a state in which the relative position with the measured object 22 is fixed, so that the measuring light 28 can be scanned in the y direction in a stabilized manner.

It should be noted that the sleeve 163 may be formed so that the entire rotating member 132 is covered therewith. In that case, it is preferable that the bottom of the sleeve 163 is fixed to the housing 471. In that case, it is also preferable that the sleeve 163 is formed of a flexible material as with the rotating member 132.

In addition, although the rotating members 131 and 132 and the sleeves 161 and 163 described above were described as being cylindrical in the illustrated examples, their shape is not limited to a cylindrical shape. For example, they may have a prism shape.

In this embodiment, the probe units 200, 203, 204 and 205 are connected to the OCT unit 100 via the flexible optical fiber 18, and thus has a hands-free configuration. In place of this configuration, it is possible to adopt a configuration in which the probe unit 200 is fixed to a stationary table or pole, or a treatment table, for example. In this case, the relative position between the probe unit 200 and the tooth, which is the measured object 22, is fixed by the measured person (patient) biting on the mouthpiece 73 of the fixed probe unit 200. Further, in this case, the measuring light 28 may not necessarily be guided between the OCT unit 100 and the probe unit 200 with the optical fiber 18, and may be guided in the air. That is, a beam splitter may be used instead of the fiber coupler 19, as will be described later in Embodiment 2. In this case, it is preferable to use a cylindrical lens to omit the mechanical manipulations in the X-axis direction or the Y-axis direction.

Further, the probe unit 200 may be fixed to the tip of a multi-articulated arm fixed to a stationary table or pole, or a treatment table. In this case, the measuring light is guided between the OCT unit 100 and the probe unit 200 with the optical fiber 18.

Embodiment 2

Figure 22:
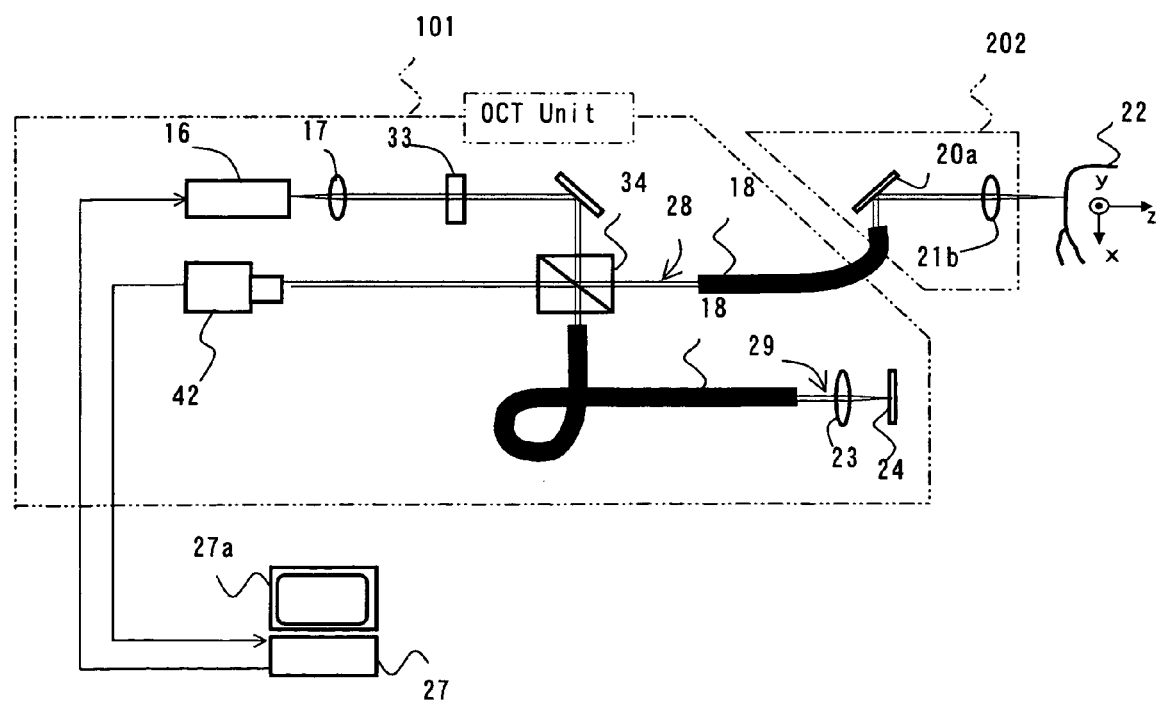
FIG. 22 is a diagram showing an example of the configuration of an FD-OCT apparatus according to Embodiment 2.

FIG. 22 is a diagram showing an example of the configuration of an FD-OCT apparatus according to Embodiment 2.

In FIG. 22, the same parts as the FD-OCT apparatus shown in FIG. 1 are denoted by the same reference numerals, and their description shall be omitted.

The FD-OCT apparatus shown in FIG. 22 differs from the FD-OCT apparatus shown in FIG. 1 in that a cylindrical lens 33 is provided, that a beam splitter 34 is used in place of the fiber coupler 19, that the galvano mirror that performs scanning in the y-axis direction is not provided, and that the photodetector 42 is a two-dimensional photodetector.

Whereas Embodiment 1 uses the method in which the galvano mirror 20b is driven is used as the method for scanning in the y-axis direction, this embodiment employs light expansion in the y-axis direction using a cylindrical lens 33 in place of the scanning of the y-axis direction using the galvano mirror 20b.

The cylindrical lens 33 is an ordinary lens with respect to its cross section in a plane including the optical axis and a direction in which the cylindrical lens 33 functions as a lens, and the shape of this cross section is the same regardless of the position of the cylindrical lens 33 in a direction in which it does not function as a lens. The cylindrical lens 33 is arranged so that the direction in which it functions as a lens is the y direction. That is, the light that has been expanded in the y direction by the cylindrical lens 33 is radiated so that it is distributed in the y direction of the measured object 22 (the y direction on the cylindrical lens 33 and the y direction of the measured object 22 are optically identical directions, and may not necessarily be spatially identical directions). The cylindrical lens 33 serves as a means for expanding the light in the y direction. The cross section of the measuring light has a linear shape along the y-axis direction.

In addition, the function similar to that of the cylindrical lens 33 also can be realized using a cylindrical mirror.

The measuring light is the light that has been spatially expanded in the y-axis direction. Therefore, in order to guide this light with the optical fiber, it is necessary that the optical fiber 18 be a bundle of optical fibers bundled so that their cross sections are arranged on a one-dimensional line, or a bundle of optical fibers bundled so that their cross sections are arranged in a two-dimensional circle. Although the measuring light 28 and the reference light 29 are guided with the optical fiber in the FD-OCT apparatus shown in FIG. 22, an optical fiber may not be necessarily used. That is, the FD-OCT apparatus may be configured to allow the measuring light 28 and the reference light 29 to be propagated spatially without using an optical fiber.

Since the measuring light 28 is radiated so that it is distributed in the y-axis direction of the measured object 22, the cross section of the measured object 22 in the y-axis direction can be obtained with the two-dimensional photodetector 42, without performing mechanical scanning in the y-axis direction. Accordingly, the three-dimensional spatial structure of the measured object 22 can be obtained only by performing scanning in the x-axis direction with the galvano mirror 20a.

As a result, the apparatus becomes simple and inexpensive, so that an FD-OCT device applicable to dental measurement can be obtained. It should be noted that the FD-OCT apparatus according to this embodiment is preferably used for dental applications. However, it is not limited to dental measurement, but also can be used for measurement for other fields. Although the FD-OCT apparatus has been described in this embodiment, the apparatus may not necessarily be an FD-OCT apparatus, but may be a conventional OCT apparatus.

Embodiment 3

Figure 23:
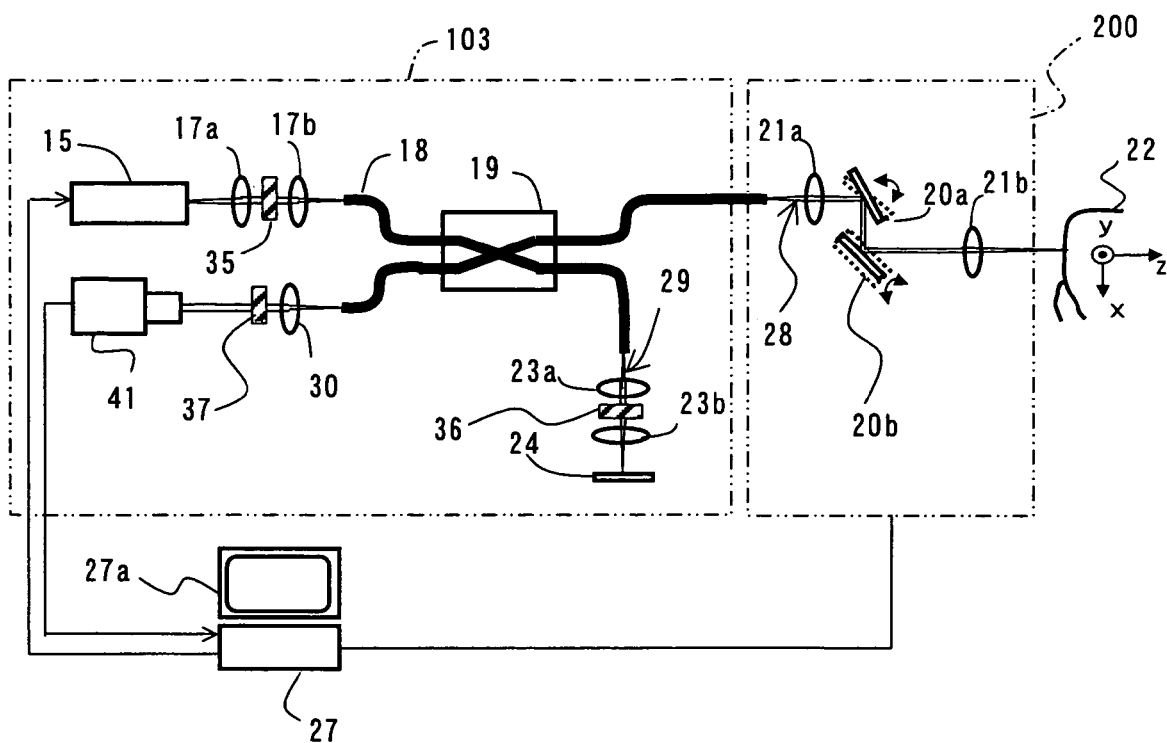
FIG. 23 is a diagram showing an example of the configuration of an FD-OCT apparatus according to Embodiment 3.

FIG. 23 is a diagram showing an example of the configuration of an FD-OCT apparatus according to Embodiment 3.

In FIG. 23, the same parts as the FD-OCT apparatus shown in FIG. 1 are denoted by the same reference numerals, and their description shall be omitted.

The FD-OCT apparatus shown in FIG. 23 differs from the FD-OCT apparatus shown in FIG. 1 in that a light-source light polarization manipulator 35, a reference light polarization manipulator 36 and an interference light polarization manipulator 37 are provided.

Figure 24A:
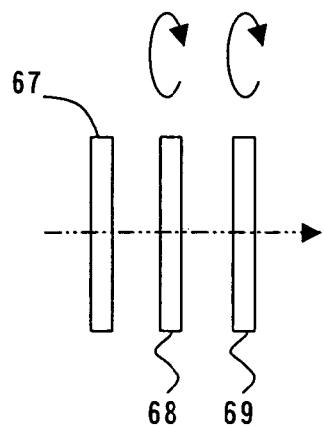
FIG. 24A is a diagram schematically showing the configuration of a light-source light polarization manipulator 35.

FIG. 24A is a diagram schematically showing the configuration of the light-source light polarization manipulator 35. In FIG. 24A, a polarizer 67 is a member that transmits only a specific polarization component therethrough, a half-wave plate board 68 is a member that shifts the wavelength of the light passing therethrough by a half wavelengths, and a quarter-wave plate 69 is a member that shifts the wavelength of the light passing therethrough by a quarter wavelength. First, the polarizer 67 imparts a basic polarization property to the light-source light or the measuring light 28. Further, the direction of polarization can be manipulated by rotating the half-wave plate 68 and the quarter-wave plate 69 at a suitable angle around the optical axis. The polarization condition of the light-source light or the measuring light can be set freely by using the wave plates 68 and 69.

Figure 24B:
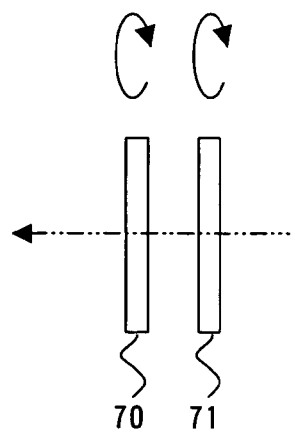
FIG. 24B is a diagram schematically showing the configuration of a reference light polarization manipulator 36 or an interference light polarization manipulator 37.

FIG. 24B is a diagram schematically showing the configuration of the reference light polarization manipulator 36 or the interference light polarization manipulator 37. These manipulators each are made up of a half-wave plate 70 and a quarter-wave plate 71, and the polarization condition of the reflected light can be examined by adjusting their angles.

Generally, the polarization condition of light can be represented by a vector having four components (four-dimensional vector) Si. When light in a certain polarization condition enters and transmits an object and is reflected in it, the polarization condition of the light changes through the interactions with the object. That is, the four-dimensional vectors S0 representing the polarization condition of the reflected light differs from the 4-dimensional vector Si representing the polarization condition of the incident light. Accordingly, the "property that changes the polarization condition (for example, birefringence property)" of the object can be represented by a 4×4 matrix M (Mueller matrix). That is, when light having a polarization condition represented by the vector Si enters a material having a birefringence property represented by the matrix M, the vector S0 representing the polarization condition of the light emitted from that material can be given by S0=M×Si.

Therefore, in order to measure the matrix M representing the birefringence property of a certain material, light having a polarization condition represented by any four vectors may be passed through the material, and the four vector components of the passed light may be detected. This Mueller matrix can be measured at each measurement point of the object.

In this embodiment, the light-source light polarization manipulator 35, which is located in the optical path of the measuring light, is operated so that the measuring light has at least four independent polarization conditions. Then, the reference light polarization manipulator 36 or the interference light polarization manipulator 37 is operated to observe the interference light resulting from the four vector components, which are the above-described polarization conditions. Thus, 16 different Mueller-matrix images can be obtained from the relationship between the above-described vector components. These images serve as the images showing the "property that changes the polarization condition=property unique to a subject" of various parts of a tomographic image of the subject.

Here, it is also possible to provide only one of the reference light polarization manipulator 36 and the interference light polarization manipulator 37 as needed.

Since body tissue, including oral tissue, has its unique polarization property, birefringence property and the like, the birefringence property of a tooth germ or periodontal tissue can be detected according to this embodiment. In particular, collagen has a large birefringence property. For example, it is possible to discriminate between enamel, which contains no collagen, and dentine, which contains a large amount of collagen. Further, 16 different images reflecting the polarization property, the birefringence property and the like unique to various parts of oral tissue can be obtained, so that it is possible to realize not only discrimination of normal tissue, but also visualization of lesion tissue, such as dental caries and congestion.

Although this embodiment has been described for an example in which a polarization light manipulator is provided in the FD-COT apparatus shown in FIG. 1, the present invention is not limited to this. For example, this embodiment is applicable also to the FD-OCT apparatus according to Embodiment 2 shown in FIG. 22.

Embodiment 4

Figure 25:
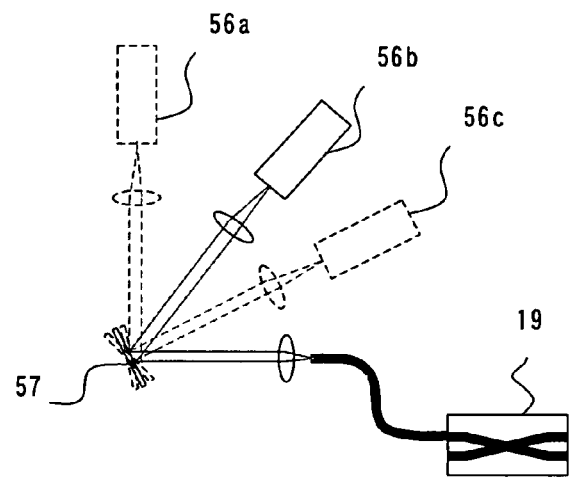
FIG. 25 is a diagram showing the configuration of a light source of the OCT apparatus.

FIG. 25 is a diagram showing an example of the configuration of a light source according to this embodiment. The light source according to this embodiment can be used for an OCT apparatus. For example, the light source 15 of the FD-OCT apparatus shown in FIG. 1 is one single-wavelength light source. On the other hand, in this embodiment, two ore more light sources 56a, 56b, and 56c respectively having different wavelengths are used in place of the light source 15. The light source 56a may be, for example, a light source having a center wavelength of 830 nm, the light source 56b may be, for example, having a center wavelength of 1300 nm and the light source 56c may be, for example, having a center wavelength of 1600 nm. The light sources 56a, 56b and 56c may be, for example, tunable LDs (laser diodes). Switching between the light sources 56a, 56b, and 56c is performed by driving a rotating mirror 57 for use by the OCT apparatus for measurement. That is, the light sources 56a, 56b, and 56c are arranged in the positions corresponding to specific angles of the rotating mirror 57. A galvano mirror may be used as the rotating mirror 57.

Incidentally, the wavelength dependencies of the absorption coefficient, the transmission coefficient and the reflection coefficient of light vary in oral tissue, oral lesion tissue, or an oral prosthetic appliance. For example, for light of a wavelength near 800 nm, the cementum and the alveolar bone have a high transmission coefficient, whereas the enamel and the dentine have a comparatively large reflection coefficient. In addition, since soft tissue such as gums has a high transmittance for light of a wavelength near 1300 nm or 1500 nm high, using such light for the light source is optimal for measurement of the alveolar bone under gums, and also tooth germ tissue located deeper therefrom. Moreover, since the fluorescence property in the visible light range in dental caries tissue differs from that of normal tissue, it is necessary to use a light source adapted to the wavelength of the fluorescence. Therefore, it has been difficult to visualize all the structures of oral tissue with conventional OCT apparatuses using a single-wavelength light source.

The OCT apparatus according to this embodiment includes the two or more light sources 56a, 56b, and 56c having different wavelengths, so that it can visualize the fine structure of materials, such as oral tissue and oral lesion tissue, having various absorption coefficients, transmission coefficients and reflection coefficient of light, for example, by selecting the wavelength of the light source appropriately. For example, although light of a longer wavelength near 1300 nm to 1500 nm cannot be scattered as easily as light of a shorter wavelength near 800 nm, it tends to be absorbed by water. Therefore, light of a longer wavelength near 1300 nm to 1500 nm can be used suitably for measurement of hard tissue such as a tooth and an alveolar bone.

In the OCT apparatus according to Embodiment 4, those parts other than the above-described parts can be applied to the OCT apparatuses according to Embodiments 1 to 3 or conventional OCT apparatuses. In addition, the light sources 56a, 56b and 56c are not limited to the tunable LD (laser diode) in the above-described example. For example, the light sources 56a, 56b and 56c may be a superluminescent diode with a wavelength in the range of 800 nm to 16000 nm.

Embodiment 5

Figure 26:
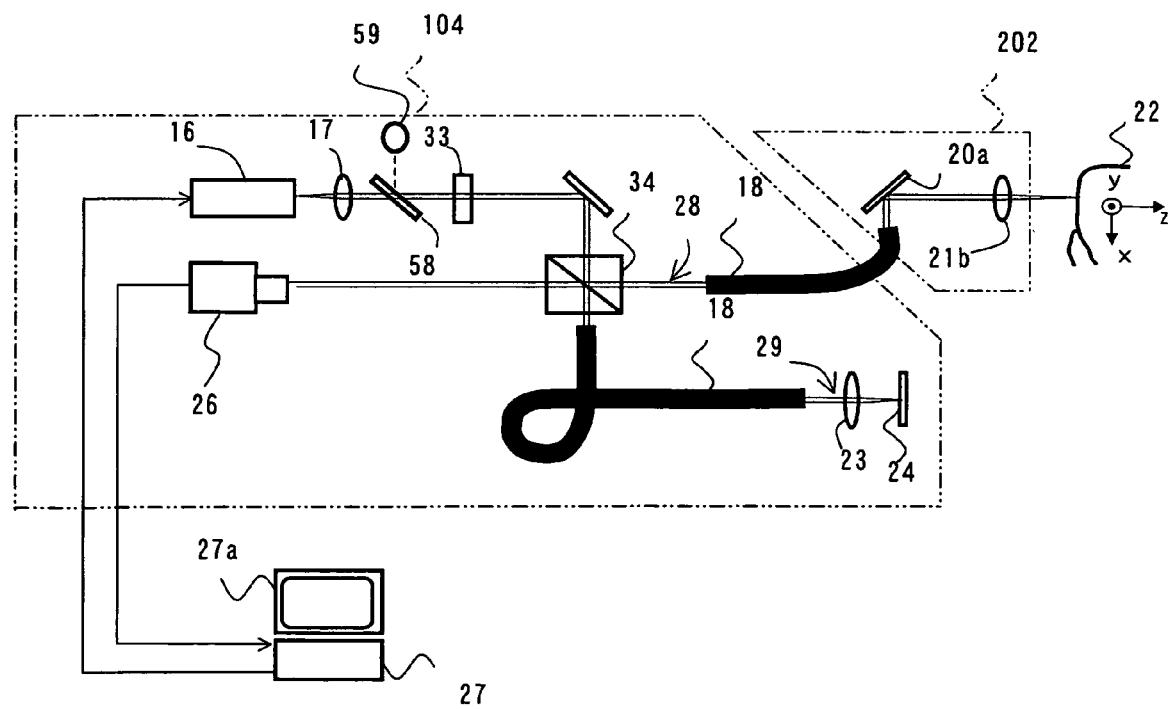
FIG. 26 is a diagram showing an example of the configuration of an FD-OCT apparatus according to Embodiment 5.

FIG. 26 is a diagram showing an example of the configuration of an FD-OCT apparatus according to Embodiment 5. In FIG. 26, the same parts as the FD-OCT apparatus shown in FIG. 22 are denoted by the same reference numerals, and their description shall be omitted. It should be noted that this embodiment is applicable not only to the FD-OCT apparatus shown in FIG. 22, but also to the FD-OCT apparatuses according to Embodiments 1 to 3 or conventional OCT apparatuses.

The FD-OCT apparatus shown in FIG. 26 differs from the FD-OCT apparatus shown in FIG. 22 in that a pilot light source 59 and half mirrors 58 and 60 are provided, and that a CCD camera 26 is provided instead of the photodetector 42.

The pilot light source 59 is provided for radiating pilot light projected to the measured object 22. Pilot light is light radiated onto an imaging region, in order for an operator performing measurement using an OCT apparatus to check an imaging area and the imaging region during imaging, or before and after imaging. Preferably, the pilot light radiated from the pilot light source 59 is visible light.

The pilot light emitted from the pilot light source 59 is guided with a half mirror 58 onto the same optical axis as the light-source light emitted from the light source 15. The pilot light is projected to the measured object 22, together with the light-source light and the measuring light. This projection can be observed visually, and allows irradiation of the same place irradiated by the measuring light, so that the operator can recognize the measuring range.

The cross section of the pilot light in a plane perpendicular to its optical axis may be in the form of dots, or may be in the form of a line. If the pilot light has a cross section in the forms of dots, then the optical axis of the pilot light is preferably arranged on the central optical axis of the measuring light. If the pilot light has a cross section in the form of a line, the above-described cross section of the pilot light preferably is arranged along the y-axis direction of the measuring light 28. Since the OCT apparatus shown in FIG. 26 uses the cylindrical lens 33, the pilot light is shaped to have a cross section in the form of a line as a result of passing through the cylindrical lens 33, and then radiated to the measured object 22.

The pilot light reflected at the measured object 22 again passes through the beam splitter 34 together with the reflected component of measuring light 28, and is radiated onto the CCD camera 26 together with the interference light. The interference light and the pilot light are detected with the CCD camera 26.

It is preferable that the CCD camera 26 serves both as a 2D-CCD camera having a sensitivity band in visible light as a two-dimensional imaging device, and a 2D-CCD camera as a two-dimensional photodetector used for FD-OCT using a cylindrical lens. Thus, together with an interference spectroscopic image of teeth obtained by using FD-OCT, a visible light image of teeth can be obtained by using the CCD camera 26.

Alternatively, a visible light image of the measured object 22 also can be obtained by providing a 2D-CCD camera having a sensitivity band in visible light as a two-dimensional imaging device separately from the CCD camera 26, and using a half mirror 60 or the like from above the optical axis of the measuring light to guide the pilot light to the 2D-CCD camera having a sensitivity band in visible light. Here, a two-dimensional imaging device having a sensitivity band at 300 nm to 3000 nm can be used as the 2D-CCD camera having a sensitivity band in visible light.

It should be noted that the optical fiber 18 is preferably constituted by image fiber capable of transmitting images.

The image of the area measured with the pilot light can be monitored at the computer 27. Further, a visual light image of the area measured with the pilot light can be recorded synchronously with a measured tomographic image.

Embodiment 6

Figure 27A:
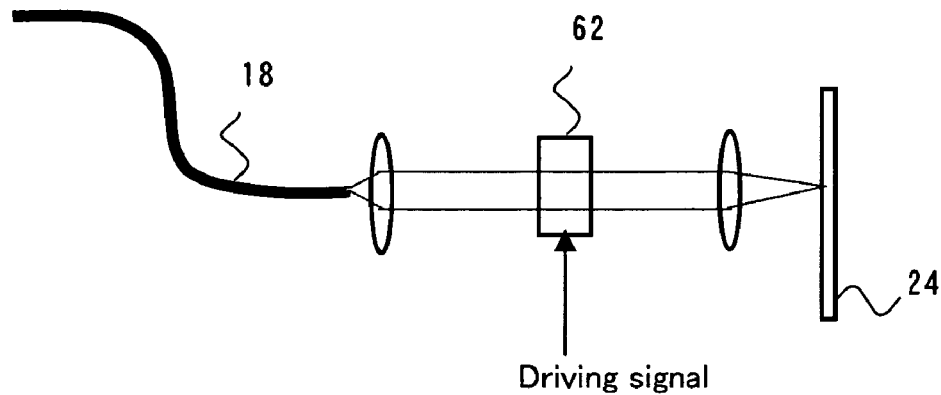
FIGS. 27A and B are diagrams showing the configuration of an OCT apparatus according to Embodiment 6 near the reference mirror.

FIG. 27 shows a configuration of an OCT apparatus according to this Embodiment 6 near the reference mirror. In the OCT apparatus according to this embodiment, the phase of the reference light is changed by inserting a phase modulation element on the optical path of the reference light, or by moving the reference mirror in the optical axis direction. FIG. 27A is a diagram showing an exemplary configuration of the apparatus in the case of inserting a phase modulation element on the optical path of the reference light. In FIG. 27A, a phase modulation element 62 is inserted in front of the reference mirror 24. The phase modulation element 62 is driven by an electric driving signal. For example, a rapid scanning optical delay line (RSOD), an acoustooptic element, an electrooptical element, etc. preferably may be used as the phase modulation element 62.

Figure 27B:
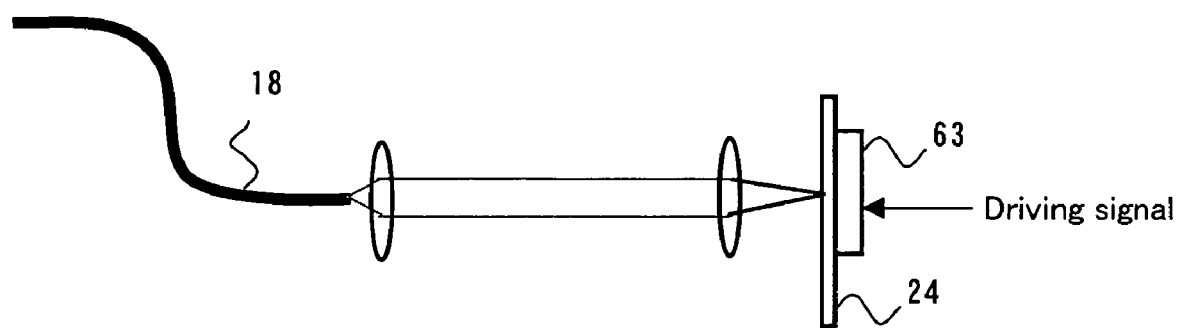

FIG. 27B is a diagram showing an exemplary configuration of the apparatus in the case of changing the phase of the reference light by moving the reference mirror in the optical axis direction. In FIG. 27B, the reference mirror 24 is provided with a piezoelectric element 63. The piezoelectric element 63 is driven by an electric driving signal. The reference mirror 24 is vibrated in the same direction as the direction of the optical axis of the reference light by the piezoelectric element 63 vibrating in the direction of the optical axis of the reference light. As a result, the phase of the reference light is changed.

According to this embodiment, the phase of the reference light can be shifted using the phase modulation element 62 or the piezoelectric element 63, so that it is possible to obtain, for example, five sets of distributions of intensity of diffracted and spectroscopically separated interference light in which the phase of the reference light is shifted by 90 degrees. By measuring the shape of the measured object in the depth direction (z-axis direction) using the distributions of diffracted and spectroscopically separated interference light intensity, the measurement range in the depth direction can be expanded twice. In the following, the principle will be described in detail.

Generally, the measuring range of FD-OCT theoretically is determined by the resolution of a diffraction element, an objective lens and a CCD camera. As a result, the measuring range in the depth direction is determined. With FD-OCT, the light intensity distribution (one- or two-dimensional) on the ξ axis of the diffraction element that has been obtained by the CCD is Fourier transformed or inverse Fourier transformed using a computer, and converted into a distribution on the time t axis (i.e., converted into a reflection property distribution on the depth z axis of the measured object). In this case, the light intensity distribution is a power spectrum, and therefore, the results of the inverse Fourier transformation are such that the autocorrelation of the reference light and a complex conjugated signal of the cross-correlation between the reference light and the light reflected in the z direction at the object will be superimposed in the distribution in the depth z-axis direction as an image (artifact) resulting from a defect of the apparatus that is unrelated to the original subject. Accordingly, measurement of the diffraction spectrometric interference image on the diffraction element will assume that not only the light intensity distribution but also the optical phase distribution have been measured, so that the measurement range in the depth direction will be half as compared with a case where perfect complex inverse Fourier transformation was performed.

There is no high-speed photodetector capable of directly detecting the phase of diffracted and spectroscopically separated interference light, because it is a phenomenon that is very rapid (a phenomenon of several femtoseconds or less, which is obtained by dividing the wavelength of light by the speed of light). Therefore, the spatial phase is modulated instead of the temporal phase, and indirect measurement of the phase of diffracted and spectroscopically separated interference light is performed equivalently. That is, for example, five sets of intensity distributions of diffraction spectroscopy interference light in which the phase of the reference light is shifted by 90 degrees can be obtained using the phase modulation element 62 or the piezoelectric element 63. By carrying out complex inverse Fourier transformation for these intensity distributions of diffraction spectroscopy interference light at the computer 27, the artifacts resulting from the autocorrelation of the reference light and the complex conjugated signal of the cross-correlation between the reference light and the light reflected in the z direction at the measured object (reflected component of the measuring light) are eliminated, and thereby an inherent measuring range in the depth direction of FD-OCT is realized.

Further, it is possible to improve the resolution by eliminating the noise by synchronous detection of the detection signal of the CCD by selecting the frequency of phase modulation appropriately, thereby expanding the measuring range further.

The FD-OCT apparatuses according to Embodiments 1 to 3 or conventional OCT apparatuses are applicable to this embodiment, except for those parts of the OCT apparatus of this embodiment other than the parts described above.

Embodiment 7

Figure 28:
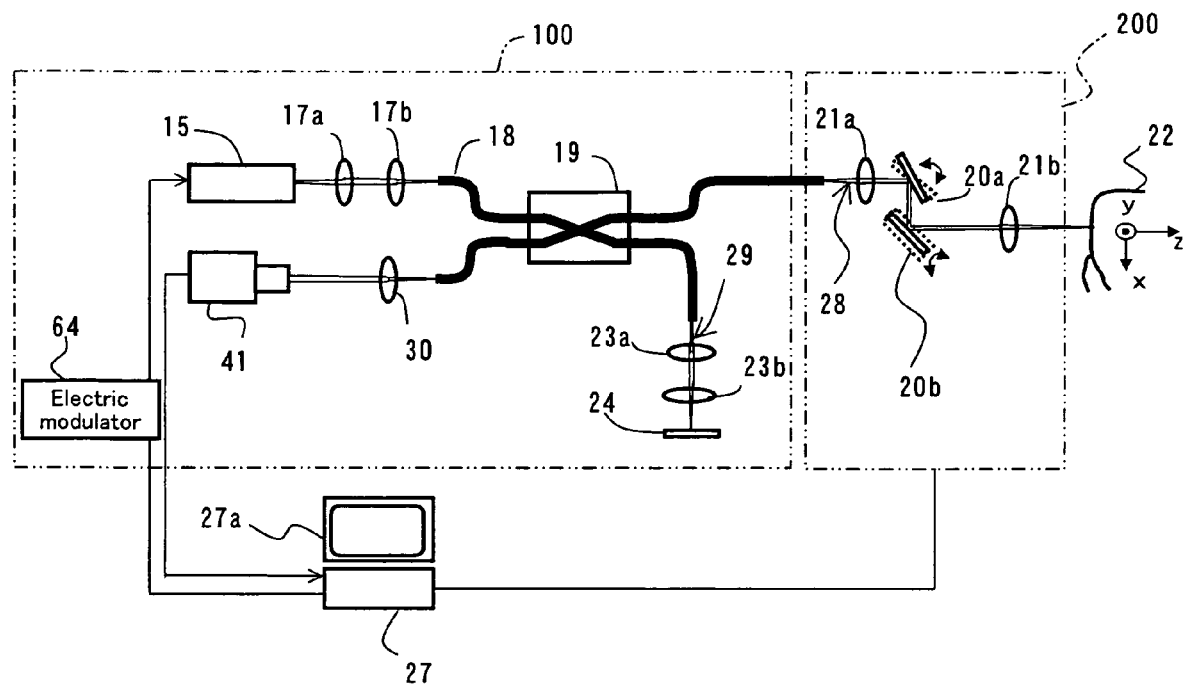
FIG. 28 is a diagram showing an example of the configuration of an FD-OCT apparatus according to Embodiment 7.

FIG. 28 is a diagram showing an example of the configuration of an FD-OCT apparatus according to Embodiment 7. In FIG. 28, the same parts as the FD-OCT apparatus shown in FIG. 1 are denoted by the same reference numerals, and their further description shall be omitted. It should be noted that this embodiment is applicable not only to the FD-OCT apparatus shown in FIG. 1, but also to the FD-OCT apparatuses according to Embodiments 1 to 3 or conventional OCT apparatuses.

The FD-OCT apparatus shown in FIG. 28 differs from the FD-OCT apparatus shown in FIG. 1 in that an electric modulator 64 is provided between a computer 27 and a light source 15.

The computer 27 sends a light quantity modulation signal to the electric modulator 64 together with an ON/OFF signal. The electric modulator 64 sends a light quantity control signal to the light source 15 based on the light quantity modulation signal. The light quantity output from the light source 15 is controlled by the light quantity control signal output from the electric modulator 64.

The data detected by the photodetector 41 is demodulated at the computer 27 in accordance with the light quantity modulation signal. The S/N ratio of the detected data is improved by this modulation and demodulation.

The method of the modulation and demodulation may be AM modulation or FM modulation, for example. It is also possible to provide a light modulator in the optical path of the light radiated from the light source 15 instead of the electric modulator 64. Alternatively, a light modulator may be provided on the optical path of the reflected component (light reflected at the object) of the measuring light 28, or on the optical path of the reference light 29. Alternatively, a modulator that performs modulation synchronized with the positions of the measured object 22 and the reference mirror 24 may be provided.

Generally, the measuring range of an OCT apparatus is narrowed by the influence of noise. That is, the measuring light attenuates as it enters the measured object 22, so that the deeper the light reflected at the object in the z direction is located in the measured object, the more likely it drowns in noise. This narrows the measuring range in the depth direction.

According to this embodiment, the light-source light, the measuring light or the reference light is modulated and a detection signal is detected, and therefore, the S/N ratio is improved and the measurable range is expanded.

Embodiment 8

Figure 29:
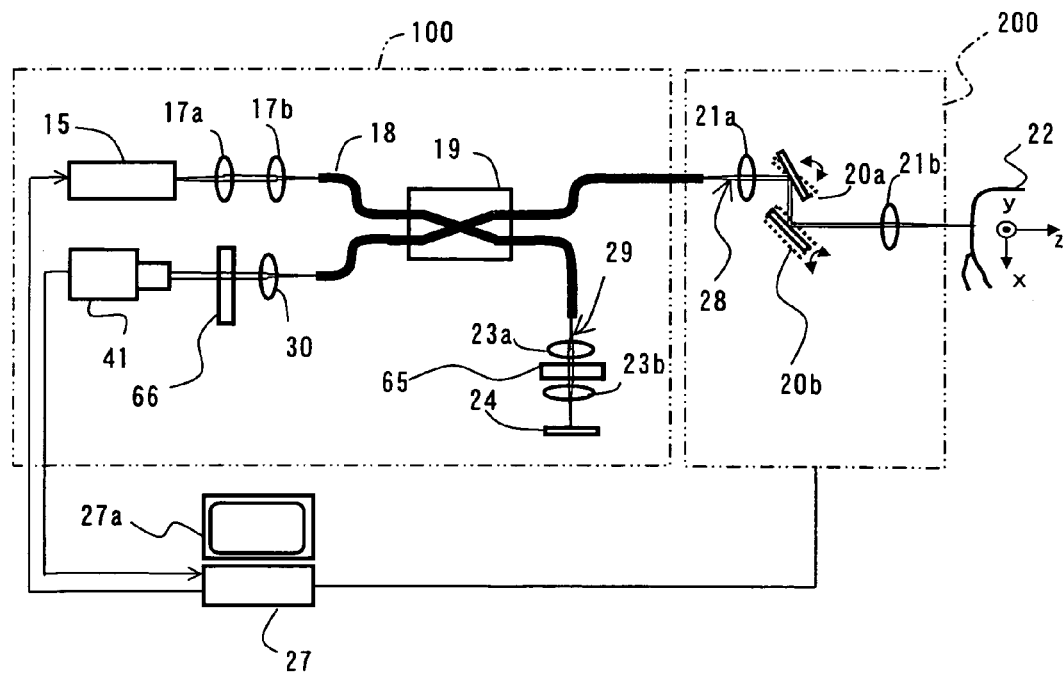
FIG. 29 is a diagram showing an example of the configuration of an FD-OCT apparatus according to Embodiment 8.
Figure 30:
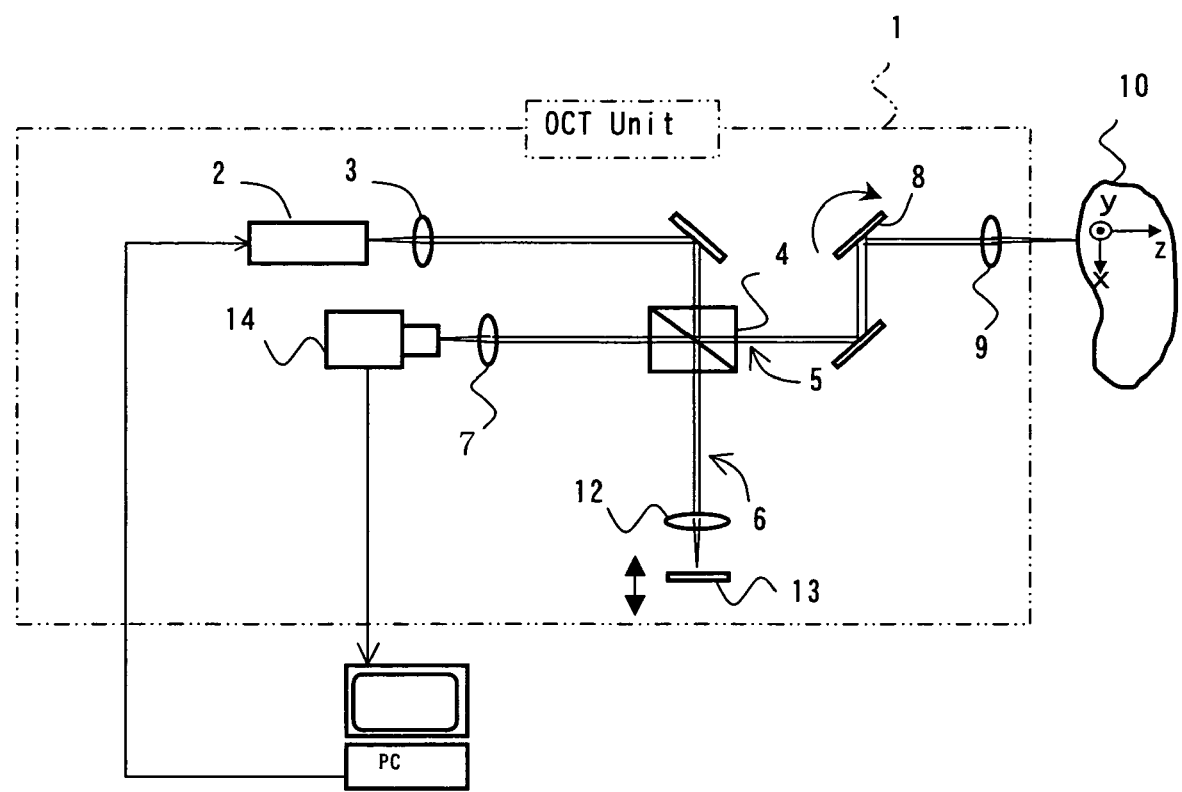
FIG. 30 is a diagram showing the configuration of a conventional OCT apparatus.

FIG. 29 is a diagram showing an example of the configuration of an FD-OCT apparatus according to Embodiment 8. In FIG. 29, the same parts as the FD-OCT apparatus shown in FIG. 1 are denoted by the same reference numerals, and their description shall be omitted. It should be noted that this embodiment is applicable not only to the FD-OCT apparatus shown in FIG. 1, but also to the FD-OCT apparatuses according to Embodiments 1 to 3 or conventional OCT apparatuses.

The FD-OCT apparatus shown in FIG. 29 differs from the FD-OCT apparatus shown in FIG. 1 in that a nonlinear optical element 65 is provided in the optical path of reference light 29, and that a filter 66 is provided. The nonlinear optical element 65 is an optical element that generates harmonics in an oscillatory waveform of light, and preferably may be a beta barium borate, for example.

Further, the filter 66 that filters out the wavelength component of the light-source light, and allows passage of a half-wavelength component of the light-source light is provided on the optical path of the interference light that has passed through the fiber coupler 19.

Generally, a living body generates fluorescence to some extent, and such fluorescence in many cases is fluorescence of secondary harmonics. In particular, this fluorescence property of tooth germ tissue often is changed by a lesion such as dental caries.

According to this embodiment, harmonics are generated in an oscillatory waveform of the reference light 29 by providing the nonlinear optical element 65 on the reference light. The secondary harmonic component included in these reference harmonics and the reflected component (light reflected in the z direction at the object) of the measuring light 28 are caused to interfere by the fiber coupler 19. As a result, the fluorescence property of the measured object 22 can be detected more clearly. Consequently, the performance of discriminating tomographic images of, for example, a lesion such as dental caries is improved.

In the following, the principle of this will be described in detail.

A living body shows a prominent second harmonic fluorescence property by two-photon absorption. This fluorescence is emitted when electrons bound to the constituent atoms of a living body leap to a high potential energy level in response to the energy equivalent to two photons of the measuring light and return from there to the original level. In the case of a living body, the potential energy level of the secondary harmonic fluorescence is close to an approximately continuous band, and the level exists in almost all wavelength bands. A characteristic of this second harmonic fluorescence lies in that fluorescence synchronized with the incident measuring light is generated, i.e., the coherence of the OCT apparatus is maintained. This second harmonic fluorescent light is emitted from the inside of the measured object 22, and a portion of it returns as the light reflected in the z direction at the object (reflected component of the measuring light 28). Meanwhile, since the nonlinear optical element 65 is provided on the path of the reference light 29, harmonics are generated in an oscillatory waveform of the reference light 29. By measuring the interference light between the reference light 29 and the light reflected in the z direction at the object (reflected component of the measuring light 28), the fluorescence property inside the measured object 22 can be detected. Therefore, this is effective in making diagnosis of a lesion, such as dental caries, that involves a change in the fluorescence property.

Embodiment 9

The FD-OCT apparatuses according to Embodiments 1 to 3 or conventional OCT apparatuses are applicable to Embodiment 9, except for the parts described below. Therefore, the description of other parts of the OCT apparatus of Embodiment 9 shall be omitted.

In an OCT apparatus, an image obtained by measurement is displayed using, for example, the display portion 27a provided in the computer 27. However, if an OCT tomographic image is displayed as it is, the image appears somewhat unnatural. In the OCT apparatus according to this embodiment, an easily viewable image can be provided by performing the following display.

When an image of the measured object is displayed, it is preferable to display a light transmitted portion, which is an area where the measuring light has enters and reached the measured object, and a portion located at a deeper area of the measured object where the measuring light has not reached so that they can be discriminated against each other.

The measuring range of the OCT apparatus in a single shot is small compared with the size of a tooth, so that it is difficult from only a single image to determine which area of the tooth was imaged and from which direction that area was imaged. Therefore, it is preferable to display a composite of a plurality of images.

Further, the distance of the measured object in the depth direction (z-axis direction) in an OCT image is an optical distance, and not an actual distance. Therefore, it is preferable to display an image for which the optical distance has been corrected to the spatial distance.

Further, since the amount of the measuring light decreases with an increase in the distance in the z direction from the surface of the measured object, the amount of the light reflected in the z direction at the object also decreases. This results in a "dark", i.e., "low reflection" area of the image when displayed. Therefore, it is preferable to display an image for which shade correction has been performed for the depth direction based on the optical distance or the integral value of the reflection amount.

In the case of displaying an image on a usual monitor screen of a PC, especially in an enlarged manner, the measurement resolution will be coarser than the resolution on the PC monitor screen, resulting in point display or point density display, or coarse gray-scale display. Therefore, it is preferable to display an image for which the display of light and dark that is achieved by the density of points has been corrected to solid display.

Since an image obtained by measurement is ultimately a tomographic image of an object, the spatial position and orientation cannot be known easily. Therefore, it is preferable to produce a stereoscopic display of the tomographic image on a pilot monitor image. It is also preferable to provide a user interface with which the operator freely can select a cross section to be displayed.

In some cases, noise may be contained in an obtained image. Therefore, it is preferable to produce a display with improved spatial resolution by eliminating temporal noise by obtaining an integrated average of a plurality of tomographic images or a plurality of images. Alternatively, it is possible to produce a display in which spatial noise has been eliminated in the x direction by obtaining an integrated average of a plurality of tomographic images obtained by scanning in the longitudinal direction (x direction). Further, it is possible to produce a display in which noise has been eliminated in the x and/or y direction by obtaining an integrated average of a plurality of tomographic images.

In addition, an image can be formed and displayed in an OCT apparatus, using an image of an intraoral camera in combination.

It should be noted that in FIGS. 1 to 16, which have been referred to in order to describe the embodiments above, the ratio of sizes or lengths of the features shown in the drawings, the focal lengths and the like do not necessarily indicate the actual ratios precisely.

As stated above, a dental OCT apparatus according to the present invention obtains information of not only the surface of a measured object, which is teeth tissue or periodontal tissue, or a dental prosthetic appliance, but also the interior thereof using light, and displays such information. That is, the present invention relates to a dental optical coherence tomography apparatus that obtains, analyzes and displays dental property data of minute area in various areas of a measured object on a measurement resolution scale.

The dental OCT apparatus according to the present invention includes an actuator for performing two-dimensional scanning in the probe unit. It is preferable that a mouthpiece or a splint is used for fixing the relative position between the probe unit and the measured object.

It is also preferable that the arithmetic portion in the dental OCT apparatus performs brightness correction in the depth direction in order to display a measured image with good visibility. Furthermore, by calculating the measurement results obtained by the measuring light of wavelengths that are temporally different, the arithmetic portion can eliminate the need of scanning in the depth direction of the measured object, or can expand the sensitivity and the measurement range. In other words, the dental OCT apparatus according to the present invention is an apparatus obtained by applying a so-called swept source OCT apparatus to dental use.

INDUSTRIAL APPLICABILITY

The present invention is applicable particularly to the field of dentistry as an inexpensive optical coherence tomography apparatus capable of high-speed measurement and having a simple configuration.

The invention claimed is:

1. A dental optical coherence tomography apparatus using tissue in a stomatognathic region of a living body or an artificial composition in the stomatognathic region as a measured object, the apparatus comprising:
    a variable wavelength light source that emits light whose wavelength changes with time;
    a light splitting portion that splits light-source light emitted from the variable wavelength light source into reference light for irradiating a reference mirror and measuring light for irradiating a measured object;
    an interference portion that causes the measuring light reflected at the measured object and the reference light reflected at the reference mirror to interfere with each other, thereby generating interference light;
    a photodetection portion that measures the interference light, whose wavelength changes with time;
    an arithmetic portion that generates reflection property data representing a position at which the measuring light is reflected at the measured object and the reflection intensity thereof by Fourier transforming or inverse Fourier transforming an intensity of the interference light measured by the photodetection portion in each stage of the changing wavelength, and that generates an image of the measured object;
    a probe that radiates the measuring light so that the measuring light is guided to the measured object, receives the measuring light reflected at the measured object, and guides the measuring light to the interference portion; and
    a fixing means that is fixed to the probe and is able to fix a relative position between the probe and the measured object by being in contact with a portion of the measured object or by being bonded thereto via an adhesive member,
    wherein the fixing means comprises a mouthpiece having a shape that can be inserted between upper dentition and lower dentition and that matches the shape of dentition including a measured object, or a splint core including a mounting portion that is attachable to an adhesive member that has a shape matching the shape of dentition including a measured object.

2. A dental optical coherence tomography apparatus using tissue in a stomatognathic region of a living body or an artificial composition in the stomatognathic region as a measured object, the apparatus comprising:
    a light source;
    a light splitting portion that splits light-source light emitted from the light source into reference light for irradiating a reference mirror and measuring light for irradiating a measured object;
    an interference portion that causes the measuring light reflected at the measured object and the reference light reflected at the reference mirror to interfere with each other, thereby generating interference light;

a photodetection portion that measures the interference light;

an arithmetic portion that generates reflection property data representing a position at which the measuring light is reflected at the measured object and the reflection intensity thereof based on the interference light measured by the photodetection portion, and that generates an image of the measured object;

a probe that radiates the measuring light so that the measuring light is guided to the measured object, receives the measuring light reflected at the measured object, and guides the measuring light to the interference portion; and a fixing means that is fixed to the probe and is able to fix a relative position between the probe and the measured object by being in contact with a portion of the measured object or by being bonded thereto via an adhesive member, wherein the fixing means comprises a mouthpiece having a shape that can be inserted between upper dentition and lower dentition and that matches the shape of dentition including a measured object or a splint core including a mounting portion that is attachable to an adhesive member that has a shape matching the shape of dentition including a measured object.

3. The dental optical coherence tomography apparatus according to claim 2, wherein the probe includes an objective lens that focuses the measuring light on the measured object, and the fixing means fixes a relative position between the probe and the measured object so that a focal point of the measuring light focused by the objective lens is located on a surface or the interior of the measured object, in a state in which the fixing member is in contact with the measured object.

4. The dental optical coherence tomography apparatus according to claim 2, wherein the probe further comprises a scanning means that scans the measuring light for irradiating the measured object in two directions perpendicular to the optical axis of the measuring light.

5. The dental optical coherence tomography apparatus according to claim 2, wherein the arithmetic portion generates reflection property data representing a depth of the measuring light entering the measured object and the reflection intensity of the measuring light at said depth based on the interference light, and corrects the reflection intensity in accordance with said depth, or a function or an integral function relating to said depth, thereby generating a tomographic image of the measured object in an optical axis direction.

6. The dental optical coherence tomography apparatus according to claim 2, wherein the arithmetic portion generates reflection property data representing a distribution of reflection intensity of the measuring light in the depth direction of the measuring light entering the measured object based on the interference light, divides the distribution of the reflection intensity into a plurality of layers in said depth direction, and correct the reflection intensity for each of the divided layers by using a transmittance of each of the divided layers to, thereby generating a tomographic image of the measured object in an optical axis direction.

7. The dental optical coherence tomography apparatus according to claim 2, wherein the light source comprises two or more light sources having different center wavelengths, and includes a light source switching portion that guides light from any one of the two or more light sources to the light splitting portion.

8. The dental optical coherence tomography apparatus according to claim 2, further comprising:

a dental shape data recording portion for recording dental shape data indicating the shape of each area of tissue in a stomatognathic region of a living body; and a display portion for displaying an image generated by the arithmetic portion, wherein the arithmetic portion extracts a portion of the generated image that represents each area, a lesion, a prosthetic appliance or a filling in the tissue in the stomatognathic region, using the dental shape data, and outputs said portion to the display portion in such a manner that said portion can be distinguished visually from other portions.

9. A dental optical coherence tomography apparatus for measuring tissue in a stomatognathic region of a living body or an artificial composition in the stomatognathic region as a measured object, the apparatus comprising:

a light source;

a light splitting portion that splits light-source emitted from the light source into reference light for irradiating a reference mirror and measuring light for irradiating a measured object;

an interference portion that caused the measuring light reflected at the measured object and the referenced light reflected at the reference mirror to interfere with each other, thereby generating interference light;

a photodetection portion that measures the interference light;

an arithmetic portion that generates reflection property data representing a position at which the measuring light is reflected at the measured object and the reflection intensity thereof based on the interference light measured by the photodetection portion, and generates an image of the measured object;

a probe that radiated the measuring light so that the measuring light is guided to the measured object, receives the measuring light reflected at the measured object, and guides the measuring light to the interference portion;

a rotating member that is attached to the probe so that it can rotate about at least one direction as a rotation axis, and that includes an irradiation port for radiating the measuring light in a direction forming a fixed angle or a variable angle with the rotation axis; and a driving portion that rotates the rotating member.

10. The dental optical coherence tomography apparatus according to claim 9, further comprising a sleeve provided on the rotating member via a bearing so that the sleeve covers the rotating member, and including a window for allowing passage of the measuring light radiated from the irradiation port.

* * * * *